(12) United States Patent
Kermekchiev et al.

(10) Patent No.: US 8,470,563 B2
(45) Date of Patent: Jun. 25, 2013

(54) USE OF WHOLE BLOOD IN PCR REACTIONS

(75) Inventors: Milko B. Kermekchiev, University City, MO (US); Wayne Morris Barnes, University City, MO (US)

(73) Assignee: DNA Polymerase Technology Inc., St. Louis, MO (US)

( * ) Notice: Subject to any disclaimer, the term of this patent is extended or adjusted under 35 U.S.C. 154(b) by 64 days.

(21) Appl. No.: 12/330,201

(22) Filed: Dec. 8, 2008

(65) Prior Publication Data

US 2009/0170060 A1    Jul. 2, 2009

Related U.S. Application Data

(60) Division of application No. 11/005,559, filed on Dec. 6, 2004, now Pat. No. 7,462,475, which is a continuation-in-part of application No. 10/850,816, filed on May 20, 2004, now abandoned.

(51) Int. Cl.
*C12P 19/34*    (2006.01)
(52) U.S. Cl.
USPC ........... 435/91.1; 435/194; 435/183; 530/350
(58) Field of Classification Search
None
See application file for complete search history.

(56) References Cited

U.S. PATENT DOCUMENTS

| | | | |
|---|---|---|---|
| 5,436,149 A | | 7/1995 | Barnes |
| 5,466,591 A | * | 11/1995 | Abramson et al. ............ 435/194 |
| 5,501,963 A | * | 3/1996 | Burckhardt .................. 435/91.2 |
| 5,616,494 A | | 4/1997 | Barnes |
| 6,428,962 B1 | * | 8/2002 | Naegele ....................... 435/6.18 |
| 6,818,431 B1 | | 11/2004 | Hong et al. |
| 7,521,178 B1 | * | 4/2009 | Asada et al. ................. 435/6.12 |

FOREIGN PATENT DOCUMENTS

| | | |
|---|---|---|
| JP | 11-501801 | 2/1999 |
| WO | 94/26766 | 11/1994 |
| WO | 01/94562 | 12/2001 |
| WO | 2004013279 | 2/2004 |
| WO | 2005/113829 | 12/2005 |
| WO | 2008/034110 | 3/2008 |

OTHER PUBLICATIONS

Akane A, Matsubara K, Nakamura H, Takahashi S, Kimura K. 1994. "Identification of the heme compound copurified with deoxyribonucleic acid (DNA) from bloodstains, a major inhibitor of polymerase chain reaction (PCR) amplification." J. Forensic Sci. 39:362-72.
Al-Soud AW, Jonsson LJ, Radstrom P. 2000. "Identification and characterization of immunoglobulin G in blood as a major inhibitor of diagnostic PCR" J. Clin. Microbiol. 38:345-50.
Al-Soud AW, Lantz P-G, Backman A, Olcen P, Radstrom P. 1998. "A sample preparation method which facilitates detection of bacteria in blood cultures by the polymerase chain reaction" J. Microbiol. Methods 32:217-224.
Al-Soud AW, Radstrom P. 1998. "Capacity of nine thermostable DNA polymerases to mediate DNA amplification in the presence of PCR-inhibiting samples." Appl. Environ. Microbiol. 64:3748-53.
Al-Soud WA, Radstrom P. 2000. "Effect of amplification facilitators on diagnostic PCR in the presence of blood, feces and meat" J. Clin. Microbiol. 38: 4463-70.
Al-Soud WA, Radstrom P. 2001. "Purification and characterization of PCR-inhibitory components in blood cells." J. Clin. Microbiol. 39:485-93.
Altwegg M, Verhoef J. 1995. "Amplification methods in diagnostic microbiology." J. Microbiol. Methods 23:3-138.
Barnes WM 1992. "The fidelity of taq polymerase catalyzing PCR is improved by an N-terminal deletion." Gene 112:29-35.
Barnes WM 1994. "PCR amplification of up to 35 kb DNA with high fidelity and high yield from bacteriophage templates." Proc. Natl. Acad. Sci., USA 91 :2216-20.
Barnes WM 1994. "Tips and tricks for long and accurate PCR" TIBS 1 9:342-46.
Baskaran N, Kandpal RP, Bhargava AK, Glynn MW, Bale A, Weissman SM. 1996. "Uniform amplification of a mixture of deoxyribonucleic acids with varying GC content" Genome Res. 6:633-8.
Bourk e MT, Scherczinger CA, Ladd C, Lee HC 1999. "NaOH treatment to neutralize inhibitors of Taq polymerase." J. Forensic Sci. 44:1046-50.
Cattaneo C, Graig OE, James NT, Bolton H. 1997. "Comparison of three DNA extraction methods on bone and blood stains up to 43 years old and amplification of three different gene sequences." J. Forensic Sci. 42:1126-35.
de Franchis R, Cross NCP, Foulkes NS, Cox TM. 1988. "A potent inhibitor of Taq polymerase copurifies with human genomic DNA." Nucleic Acids Res. 16:10355.
Frackman S, Kobs G, Simpson D, Storts D. 1998. "Betaine and DMSO: enhancing agents for PCR." Promega Notes 65:27.
Ghadessy FJ, Ong JL, Holliger P. 2001. "Direct evolution of polymerase function by compartmentalized self-replication." Proc. Natl. Acad. Sci., USA 98:4552-57.
Izraeli S, Pfleiderer C, Lion T. 1991. "Detection of gene expression by PCR amplification of RNA derived from frozen heparinized whole blood." Nucleic Acids Res. 19:6051.
Kellogg DE, Rybalkin I, Chen S, Mukhamedova N, Vlasik T, Siebert PD, Chenchik A. 1994. "TaqStart Antibody: "hot start" PCR facilitated by a neutralizing monoclonal antibody directed against Taq DNA polymerase" Biotechniques 16:1134-7.
Kermekchiev MB, Tzekov A, Barnes WM 2003. "Cold-sensitive mutants of Taq DNA polymerase provide a hot start PcR." Nucleic Acids Res. 31 :6139-47.
Klein A, Barsuk R, Dagan S, Nusbaum O, Shouval D, Galun E. 1997. "Comparison of methods for extraction of nucleic acid from hemolytic serum for PCRamplification of hepatitis B virus DNA sequences." J. Clin. Microbiol. 35:1897-99.
Kox LF, Rhienthong D, Miranda AM, Udomsantisuk N, Ellis K, van Leeuwven J, van Heusden S, Kuijper S, Kolk AH 1994. "A more reliable PCR for detection of Mycobacterium tuberculosis in clinical samples" J. Clin. Microbiol. 32:672-80.
Kramvis A, Bukovzer S, Kew MC 1996. "Comparison of hepatitis B virus DNA extractions from serum by the QIAamp blood kit, Genereleaser, and the phenolchloroform method." J. Clin. Microbiol. 34:2731-33.

(Continued)

*Primary Examiner* — Richard Hutson
(74) *Attorney, Agent, or Firm* — Dentons US LLP

(57) ABSTRACT

A method of obtaining DNA amplification of a nucleic acid target from a volume of whole blood comprising performing DNA amplification in a PCR assay mixture with a blood-resistant polymerase.

20 Claims, 9 Drawing Sheets

OTHER PUBLICATIONS

Kreader CA. 1996. "Relief of amplification inhibition in PCR with bovine serum albumin or T4 gene 32 protein." Appl. Environ. Microbiol. 62:1102-06.

Lantz P-G, Al-Soud WA, Knutsson R, Hahn-Hagerdal B, Radstrom P. 2000. Biotechnical use of the polymerase chain reaction for microbial analysis of biological samples, p. 87-130, In M.R. El-Gewely (ed.), Biotechnology Annual Review, vol. 5.

Morata P, Queipo-Ortuno I, Colmenero J. 1998. "Strategy for optimizing DNA amplification in a peripheral blood PCR assay used for diagnosis of human brucellosis" J. Clin. Microbiol. 36: 2443-46.

Rossen L, Neskov P, Holmstr~ImK, Rasmussen OF. 1992. "Inhibition of PCR by components of food samples, microbial diagnostic assays and DNA-extraction solution." Int. J. Food Microbiol. 17:37-45.

Scalice ER, Sharkey DJ, Daiss JL. 1994. "Monoclonal antibodies prepared against the DNA polymerase from Thermus aquaticus are potent inhibitors of enzyme activity" J. Immunol. Methods 172:147-63.

Sharkey DJ, Scalice ER, Christy KG Jr, Atwood SM, Daiss JL. 1994. "Antibodies as thermolabile switches: high temperature triggering for the polymerase chain reaction." Biotechnology 12506-9.

Tabor S, Richardson CC 1995. "A single residue in DNA polymerases of the *E. coli* DNA polymerase I family is critical for distinguishing between deoxy- and dideoxyribonucleotides." Proc. Natl. Acad. Sci., USA 92:6339-43.

Tawfik DS, Griffiths AD 1998. "Man-made cell-like compartments for molecular evolution." Nature Biotech. 16:652-56.

Topal MD, Sinha NK. 1983. "Products of bacteriophage T4 genes 32 and 45 improve the accuracy of DNA replication in vitro." J. Biol. Chem. 258:12274-79.

Wilson IG 1997. "Inhibition and facilitation of nucleic acid amplification." Appl. Environ. Microbiol. 63:3741-51.

Panaccio M. et al., "PCR based diagnosis in the presence of 8% (v/v) Blood" Nucleic Acids Research, Oxford University Press, Surrey GB, vol. 19, No. 5 1991.

Xiao Yan Zhong et al. "Sensitive and specific detection of carcinoembryonic antigen CDNA using the hot start polmerase chain reaction technique" Clinical Laboratory Publications, Heidelberg. vol. 46, No. 1/02 (2000).

Burckhardt, J. "Amplification of DNA from Whole Blood" PCR Methods & Applications, Cold Spring Harbor Laboratory Press, US, vol. 3, No. 4 (1994).

European Search Report issued on Dec. 12, 2008 in connection with corresponding European Patent Application No. 05759554.8.

GenBank Accession No. J04639, Webpage last accessed Aug. 28, 2009.

Gundry et al., "Amplicon melting analysis with labeled primers: a closed-tube method for differentiating homozygotes and heterozygotes." Clin. Chem., 2003, 49:396-406.

Lamontagne et al., "Evaluation of extraction and purification methods for obtaining PCR-amplifiable DNA from compost for microbial community analysis." J. of Microbiol. Methods, 2002, 49:255-264.

Lawyer et al., "Isolation, Characterization, and Expression in *Escherichia coli* of the DNA polymerase gene from Thermus aquaticus." J Biol Chem, 1989, 254:6427-37.

Link et al., "Beyond toothpicks: new methods for isolating mutant bacteria." Nature Reviews, 2007, 5(9):680-688.

Monis et al., "Comparison of SYTO9 and SYBR Green I for real-time polymerase chain reaction and investigation of the effect of dye concentration on amplification and DNA melting curve analysis." Anal. Biochem., 2005, 340:24-34.

Nath et al., "Effects of ethidium bromide and SYBR Green I on different polymerase chain reaction systems." J. Biochem. Biophys. Methods, 2000, 42:15-29.

Sanger et al., "Rapid filter assay for the detection of DNA polymerase activity: direct identification of the gene for the DNA polymerase from Thermus aquaticus." Gene, 1991, 97(1), 119-123.

Stubner, "Enumeration of 16S rDNA of Desulfotomaculum lineage 1 in rice field soil by real-time PCR with SybrGreen™ detection." J. Microbiol. Methods, 2002, 50:155-64.

Tsai et al., "Rapid method for separation of bacterial DNA from humic substances in sediments for polymerase chain reaction." Environ. Microbiol., 1992, 58:2292-2295.

Watson and Blackwell, "Purification and characterization of a common soil component which inhibits the polymerase chain reaction." Can. J. Microbiol., 2000, 46:633-642.

Yeates et al., "Methods for microbial DNA extraction from soil for PCR amplification." Biol. Proced. Online, 1998, 1:40-47.

Europe Office Action dated Feb. 16, 2011 in related Application No. 05759554.8.

Kermekchiev et al., Mutants of Taq DNA polymerase resistant to PCR inhibitors allow DNA amplification from whole blood and crude soil samples, Nucleic Acids Research, 2009, 14 pages, vol. 37, No. 5.

Canadian Office Action dated Jul. 31, 2012 in related Application No. 2,567,620, 5 pages.

Akishev et al., Thermostable DNA polymerase from Thermus thermophilus B35: Cloning, sequence analysis, and gene expression, Biochemistry (Moscow), 1999, 64(11):1298-1304.

Ignatov et al., Substitution of Asn for Ser(543) in the large fragment of Taq DNA polymerase increases the efficiency of synthesis of long DNA molecules, FEBS Letters, 1998, 425:249-250.

Myers and Gelfand, Reverse transcription and DNA amplification by a Thermus thermophilus DNA polymerase, Biochemistry, 30(31):7661-7666, Aug. 1991.

Office Action issued by the European Patent Office in application No. EP 05759554.8, Mar. 2010.

Japanese Office Action dated Dec. 21, 2010 in related Application No. JP2007-527461, in Japanese.

Japanese Office Action dated Dec. 21, 2010 in related Application No. JP2007-527461, in English.

Japanese Publication No. JP11-501801, published Feb. 16, 1999, abstract only, in English.

\* cited by examiner

USE OF WHOLE BLOOD IN PCR REACTIONS

CROSS-REFERENCE TO RELATED APPLICATIONS

The present application is a Divisional of U.S. application Ser. No. 11/005,559, filed on Dec. 6, 2004, which is a continuation-in-part of U.S. application Ser. No. 10/850,816, filed May 20, 2004, each incorporated herein by reference in their entirety to the extent permitted by law, and claims benefit of priority therefrom.

INCORPORATION BY REFERENCE OF SEQUENCE LISTING

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

BACKGROUND

The polymerase chain reaction (PCR) is a sensitive DNA amplification procedure that permits the selection and detection of specific nucleic acids from a complex mixture. In its most rudimentary form, PCR is employed using a sample that contains a target nucleic acid (DNA), a set of DNA primers that hybridize to the target, and a DNA polymerase that is capable of primer-based synthesis of complementary strands of the target. During the nucleic acid amplification process, the target:primer:polymerase mixture is subjected to successive rounds of heating at different temperatures to facilitate target DNA strand separation (performed at 90-99° C.), primer:target DNA strand annealing (performed at ~40-70° C.), and DNA polymerase-mediated primer elongation (performed at ~50-72° C.) to create new complementary target strands. Because the reaction may be subjected to ~25-45 rounds of cycling to yield the desired DNA amplification product, PCR is usually conducted using thermostable DNA polymerases that can withstand the very high temperatures associated with target strand separation without suffering inactivation due to heat-induced protein denaturation. Since its introduction in the mid-1980's, PCR has become the de facto standard for detecting minute quantities of nucleic acids in samples, and obtaining specific genes from complex DNA genomes and samples.

A major problem with diagnostic and forensic techniques based on PCR is the false-negative reactions or low sensitivity caused by inhibitory substances that interfere with PCR (1, 2, 3). Of particular clinical importance is the PCR analysis of blood samples, which represents the largest fraction of human health related tests for diagnosis of genetic diseases, virus and microbial infections, blood typing, and safe blood banking. Various studies indicate that the inhibitory effect of blood on PCR is primarily associated with direct inactivation of the thermostable DNA polymerase and/or capturing or degradation of the target DNA and primers. It has been reported that the protease activity in blood also contributes to the reduced efficiency of PCR (1-5, 7, 10, 12).

The blood resistance characteristics of the thermostable DNA polymerases vary with the source of the enzyme (6). Widely used thermostable polymerases like *Thermus aquaticus* DNA polymerase (Taq) and AmpliTaq Gold® are completely inhibited in the presence of 0.004-0.2% whole human blood (vol/vol; 3, 4, 6). Various agents have been tested for reducing the inhibitory effect of blood on Taq. It was found that an addition of betaine, bovine serum albumin, the single-stranded DNA binding protein of the T4 32 gene (gp 32), or a cocktail of protease inhibitors can partially relieve the blood inhibition and allow Taq to work in up to 2% blood (vol/vol), although this effect could be sample specific (3, 8, 9, 11).

Several major inhibitors of PCR in human blood have been characterized such as immunoglobulin G, hemoglobin, lactoferrin and excess of leukocyte DNA (4, 7, 10). The IgG, hemoglobin, and lactoferrin have been purified from plasma, erythrocytes and leukocytes, respectively, using size-exclusion and anion-exchange chromatography (4, 7). The heme has been reported to inactivate the Taq polymerase by binding to its catalytic domain (10), while the mechanism of action of the other inhibitory components is more poorly understood. The inhibitory effect of IgG can be reduced when this plasma fraction is heated at 95° C. before adding it to PCR, or with the addition of excess non-target DNA to the PCR mixture. However, heating of IgG together with target DNA at 95° C. was found to block amplification. Inhibition by IgG may be due to an interaction with the single-stranded DNA fraction in the target DNA. The inhibitory effect could be removed also by treating the plasma with DNA-agarose beads prior to amplification (4).

Other complicating factors include EDTA and heparin, used as anti-coagulants, which can also inhibit DNA amplification. The addition of heparinase has been shown to counteract the heparin-mediated inhibition (13, 14). Therefore, various laboratory procedures of sample preparation have been developed to reduce the inhibitory effect of blood. The DNA purification methods suitable for PCR can include additional steps like dialysis, treatment with DNA-agarose beads or Chelex 100 resin, multiple DNA washes, or a combination of dilution with buffer which causes lysis of red blood cells, centrifugation to recover the white blood cells, washing with NaOH and the addition of bovine serum albumin (2,3, 15-19).

These pre-treatment steps of the blood samples are generally time-consuming, labor-intensive, and can be sample specific. The guanidinium thiocyanate method for DNA isolation is not suitable for reliable detection of Mycobacterium tuberculosis in clinical samples. An alternative method of DNA purification with protease K treatment followed by phenol-chloroform extraction has to be employed to relieve the inhibition (20). Separation with a QIAamp kit followed by dialysis with a Millipore filter are required for eliminating the heme inhibition of hepatitis B virus detection (21). In addition, some the above steps carry a risk of target DNA losses and are not suitable for automation. Moreover, even commercial kits specially formulated for DNA purification from blood samples such as QIAmp or GeneReleaser are not always satisfactory. The reason is due to an incomplete removal of Taq inhibitors, which can result in false-negative results. For example, 14% of the human blood samples tested for hepatitis B virus yielded false-negative results when using such blood kits (21).

The objective of achieving specificity of amplification reactions for samples containing whole blood is further complicated by two types of unwanted DNA synthesis reactions that occur during PCR. Both types of side-reactions are frequently competitive with the desired target and can lead to impure product or failed amplification. This is particularly problematic for PCR assays containing a low copy number of the nucleic acid template target, wherein the PCR conditions are modified to include a greater number of amplification cycles to achieve an adequate yield of the desired amplification product.

The first type of unwanted DNA synthesis is priming on less specific sequences in the template. This is only an issue if the template is contaminated with single-stranded nucleic acid or if the template is single-stranded, which is the case if the DNA preparation has been subjected to melting conditions during its isolation.

The second type of unwanted DNA synthesis is primers acting as templates for themselves and/or each other, with at least the result of modifying their 3' ends by the addition of additional nucleotides. These so-modified primers are able to anneal to the nucleic acid target; however, they do not serve as primers for complementary strand synthesis due to the presence of mismatched nucleotides at the site of elongation between the 3' end of the primer and the desired target. This problem is often referred to as "primer dimer", although this name is not accurately descriptive. This problem can often be reduced or avoided by careful primer design, and it is more of a problem with multiplex PCR, since there is more opportunity for accidental homology among multiple pairs of primers.

A procedure known as "hot start PCR" avoids the occurrence of both types of unwanted DNA synthesis side-reactions. According to this method, the enzyme DNA polymerase, or a buffer component essential to its activity, such as the magnesium (II) cation and/or the dNTPs, is withheld from the other PCR assay mixture ingredients until the PCR reaction has been heated to at least the normal primer-annealing (or, preferably, the DNA extension) temperature (55-75° C., optimal 68° C.). At this temperature the primers can presumably not form stable duplexes with themselves or at unwanted template sequences. After the selective temperature is achieved, the omitted component is added to reaction to reconstitute a functional amplification mixture.

Typical hot start PCR procedures are not only labor-intensive, they expose the PCR reactions to contamination with each other and with molecules that have been previously amplified in the thermal cycler machine.

The more standard ways of executing a hot start consist of formulating the PCR reaction in two parts, such that the DNA polymerase is not able to act on the DNA until the two portions are combined at high temperature, usually 65-85° C. For instance, an initial solution containing all of the magnesium is introduced to the reaction tube encapsulated in a wax bead or sealed under a layer of wax. The rest of the reaction, without Mg, is then added, along with an overlay of oil, if appropriate. While the reaction heats for the first cycle, the wax melts and floats to the surface, allowing the magnesium to mix with the reaction volume. The DNA polymerase activity is therefore reconstituted at a temperature that does not allow non-specific or unwanted primer interactions. A great drawback to the wax method comes after the PCR cycling is complete, and the product must be withdrawn for analysis. The wax then tends to plug the pipette tip, greatly adding to the time and effort of reaction analysis.

Recently, a method of hot start which is not hot at all, but which uses anti-Taq antibodies, has been described, patented and made commercially available (33-35). The antibodies largely neutralize the enzyme activity of the Taq polymerase, and can be added any time prior to the primers, or be conveniently present during storage of the stock enzyme. The antibodies are thermolabile, thus permitting the Taq polymerase to resume activity after the first heat step. The antibodies so far developed for this method must be used in 10-fold molar excess and are expensive. Furthermore, the antibodies inhibit some long PCR assays that are conducted with the KlentaqLA polymerase mixture.

A chemically inactivated form of the Taq polymerase has been introduced recently, termed AmpliTaq Gold®. The nature of the inactivation is proprietary, but the inactivation is reversible by heating the polymerase at 95° C. This method may be even more convenient than the other methods, but it has at least one current disadvantage: the time for reactivation is about 10 minutes at 95° C. This procedure is incompatible with long PCR applications, as this treatment would excessively depurinate nucleic acid targets longer than a few kb.

Thus, the analysis of whole blood samples using PCR would be benefited by the discovery of new reagents and methods that overcome the aforementioned shortcomings of current PCR technologies. The invention disclosed herein addresses and solves many of these shortcomings.

SUMMARY OF THE INVENTION

In a first aspect, the present invention is a method of obtaining DNA amplification of a nucleic acid target from a volume of whole blood comprising performing DNA amplification in a PCR assay mixture with a blood-resistant polymerase.

In a second aspect, the present invention is a method of obtaining DNA amplification of a nucleic acid target from a volume of whole blood comprising performing DNA amplification in a PCR assay mixture with KT-1(SEQ ID NO:2) or Z-TAQ™.

In a third aspect, the present invention is a method of obtaining DNA amplification of a nucleic acid target from a whole blood sample with a DNA amplification cocktail by avoiding mixing of the whole blood sample with the DNA amplification cocktail in a reaction vessel before thermal cycling that includes the following steps: adding the DNA amplification cocktail to the reaction vessel, wherein the DNA amplification cocktail comprises at least one DNA polymerase; adding the whole blood sample to the reaction vessel, wherein the whole blood sample is layered beneath the DNA amplification cocktail regardless of the order of addition of the DNA amplification cocktail and the whole blood sample to the reaction vessel; and performing a thermal cycling program to effect DNA amplification of the nucleic acid target.

In a fourth aspect, the present invention is a method of obtaining a hot start for DNA amplification of a nucleic acid target that includes the preparation of the reaction cocktail comprising at least a first volume component and a second volume component. The second volume component is heavier than the first volume component. The first volume component comprises a DNA polymerase cocktail lacking an essential constituent required for DNA amplification activity. The second volume component includes the essential constituent required for DNA amplification activity. The second volume component is underlayed below the first volume component without undue mixing before a DNA amplification reaction is initiated.

In a fifth aspect, the present invention is an isolated polypeptide comprising an amino acid sequence having at least 80% amino acid sequence identity with at least one member selected from the group consisting of KT-6 (SEQ ID NO:4), KT-7 (SEQ ID NO:6), KT-10 (SEQ ID NO:20), KT-12 (SEQ ID NO:24), FL-10 (SEQ ID NO:28), and FL-12 (SEQ ID NO:30), wherein the isolated polypeptide comprises a blood-resistant polymerase.

In a sixth aspect, the present invention is an isolated polypeptide comprising a amino acid sequence having at least 80% amino acid sequence identity with at least one member selected from the group consisting of KT-7 (SEQ ID NO:6), KT-11 (SEQ ID NO:22), KT-12 (SEQ ID NO:24), and FL-12 (SEQ ID NO:30), wherein the isolated polypeptide comprises a faster elongating polymerase.

In a seventh aspect, the present invention is an isolated polypeptide comprising at least one member selected from the group consisting of KT-6 (SEQ ID NO:4), KT-7 (SEQ ID NO:6), KT-10 (SEQ ID NO:20), KT-11 (SEQ ID NO:22), KT-12 (SEQ ID NO:24), FL-10 (SEQ ID NO:28), and FL-12 (SEQ ID NO:30).

In an eighth aspect, the present invention is an isolated polypeptide comprising KT-1 (SEQ ID NO:2) having at least two amino acid residue substitutions, wherein one of the at least two amino acid residue substitutions comprises amino acid residue position 430 such that the isolated polypeptide encodes a blood-resistant polymerase, a faster elongating polymerase, or a blood-resistant, faster elongating polymerase.

In a ninth aspect, the present invention is an isolated polypeptide comprising Taq DNA polymerase (SEQ ID NO:26) having at least three amino acid residue substitutions, wherein one of the at least three amino acid residue substitutions comprises amino acid residue position 708 such that the isolated polypeptide encodes a blood-resistant polymerase, a faster elongating polymerase, or a blood-resistant, faster elongating polymerase.

In a tenth aspect, the present invention is an isolated nucleic acid comprising a nucleotide sequence having at least 80% nucleotide sequence identity with at least one member selected from the group consisting of KT-1 (SEQ ID NO:1), KT-6 (SEQ ID NO:3), KT-7 (SEQ ID NO:5), KT-10 (SEQ ID NO:19), KT-12 (SEQ ID NO:23), Taq DNA polymerase (SEQ ID NO:25), FL-10 (SEQ ID NO:27), and FL-12 (SEQ ID NO:29), wherein the isolated nucleic acid encodes a blood-resistant polymerase.

In an eleventh aspect, the present invention is an isolated nucleic acid comprising a nucleotide sequence having at least 80% nucleotide sequence identity with at least one member selected from the group consisting of KT-1 (SEQ ID NO:1), KT-7 (SEQ ID NO:5), KT-11 (SEQ ID NO:21), KT-12 (SEQ ID NO:23), Taq DNA polymerase (SEQ ID NO:25), and FL-12 (SEQ ID NO:29), wherein the isolated nucleic acid encodes a faster elongating polymerase.

In a twelfth aspect, the present invention is an isolated nucleic acid comprising at least one member selected from the group consisting of KT-6 (SEQ ID NO:3), KT-7 (SEQ ID NO:5), KT-10 (SEQ ID NO:19), KT-11 (SEQ ID NO:21), KT-12 (SEQ ID NO:23), FL-10 (SEQ ID NO:27), and FL-12 (SEQ ID NO:29).

In a thirteenth aspect, the present invention is an isolated nucleic acid comprising KT-1 (SEQ ID NO:1) having at least two codon substitutions, wherein one of the at least two codon substitutions comprises codon position 430 such that the isolated nucleic acid encodes a blood-resistant polymerase, a faster elongating polymerase, or a blood-resistant, faster elongating polymerase.

In a fourteenth aspect, the present invention is an isolated nucleic acid comprising Taq DNA polymerase (SEQ ID NO:25) having at least three codon substitutions, wherein one of the at least three codon substitutions comprises codon position 708 such that the isolated nucleic acid encodes a blood-resistant polymerase, a faster elongating polymerase, or a blood-resistant, faster elongating polymerase.

In a fifteenth aspect, the present invention is a method of obtaining rapid DNA amplification of a nucleic acid target in a PCR assay mixture comprising a faster elongating DNA polymerase.

In a sixteenth aspect, the present invention is a kit for performing PCR assays on samples of whole blood, wherein the kit comprises a blood-resistant polymerase.

In a seventeenth aspect, the present invention is a kit for performing PCR assays on samples of whole blood, wherein the kit comprises KT-1 (SEQ ID NO:2) or Z-TAQ™.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

ABBREVIATIONS AND DEFINITIONS

Figure 1:
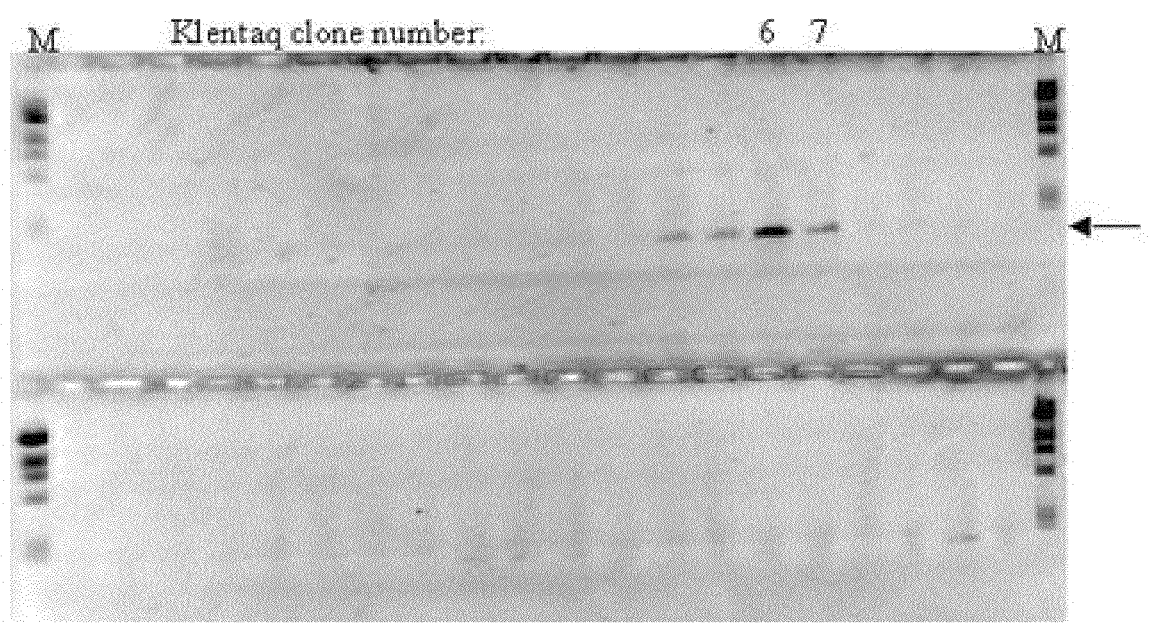
FIG. 1 depicts results of PCR assays with different forms of Klentaq polymerase (40 mutants and wild-type form of Klentaq) conducted in the presence of inhibitory amounts of blood. Clones KT-6 and KT-7 were capable of amplifying a 1.65 kbp target DNA from added plasmid template in the presence of 10% whole human blood.

The following definitions and methods are provided to better define the present invention and to guide those of ordinary skill in the art in the practice of the present invention. Unless otherwise noted, terms are to be understood according to conventional usage by those of ordinary skill in the relevant art.

The term "amplicon" refers to the nucleic acid that is the target of DNA amplification of a PCR assay.

The phrase "amplification activity" refers to the functional ability of a DNA polymerase to synthesize copies of a nucleic acid target under the PCR conditions disclosed herein to yield a quantity of amplified DNA product that is discernable by intercalative dye (e.g., ethidium bromide) staining methods that are well known in the art.

The phrase "homogeneous PCR assay solution" as used herein refers to a solution that is homogenous with respect to the absence of discrete phases. A homogeneous PCR assay solution is one that is typically prepared by mixing the contents of a reaction vessel using a vortexer or comparable mixing apparatus. In the context of heavy hot start PCR assays, the PCR assay solution is composed of two phases prior to initiating the thermal cycling program; that is, the PCR assay solution of a heavy hot start PCR assay is not premixed prior to initiating a thermal cycling program and is not considered a homogenous PCR assay solution.

The phrase "blood-resistant polymerase" as used herein refers to a mutant form of either Klentaq-278 DNA polymerase or full-length Taq DNA polymerase wherein the mutant enzyme is cold sensitive and displays amplification activity in a homogeneous PCR assay solution containing whole blood in the range from about 3% (vol/vol) to about 25% (vol/vol). By "cold sensitive," the mutant enzyme displays lower amplification activity than wild-type Taq DNA polymerase at reduced temperatures relative to the normal temperature at which DNA extension reactions are performed (~72° C.). Such a mutant enzyme displays DNA amplification activity under hot start PCR conditions. A mutant form of Klentaq-278 DNA polymerase includes a polypeptide that does not encode the identical amino acid sequence of Klentaq-278 DNA polymerase (SEQ ID NO:2). Examples of such mutant forms include a deletion of at least one amino acid, an insertion of additional amino acids, or a change of at least one amino acid relative to the amino acid sequence of the Klentaq-278 DNA polymerase (SEQ ID NO:2). A mutant form of full-length Taq DNA polymerase includes a polypeptide that does not encode the identical amino acid sequence of the full-length Taq DNA polymerase (GenBank Accession No. J04639; SEQ ID NO:25). Examples of such mutant forms include a deletion of at least one amino acid, an insertion of additional amino acids, or a change of at least one amino acid relative to the amino acid sequence of the full-length Taq DNA polymerase (SEQ ID NO:25).

The phrase "faster elongating polymerase" as used herein refers to a derivative of Taq DNA polymerase that displays amplification activity in PCR assays conducted with extension times in the range from about 12 seconds to about 50 seconds to complete up to 2 kb.

The phrase "physiologically compatible buffer" as used herein refers to any solution that is compatible with the function of enzyme activities and enables cells and biological macromolecules to retain their normal physiological and biochemical functions. Typically, a physiologically compatible buffer will include a buffering agent (e.g., TRIS, MES, PO4, HEPES, etc.), a chelating agent (e.g., EDTA, EGTA, or the like), a salt (e.g., NaCl, KCl, MgCl2, CaCl2, NaOAc, KOAc, Mg(OAc)2, etc.) and optionally a stabilizing agent (e.g., sucrose, glycerine, Tween20, etc.).

The polymerases referred to throughout this description have the following structures and properties: (1) Taq refers to the wild-type, full-length DNA Polymerase from *Thermus aquaticus* (GenBank Accession No. J04639) and also used for chemically modified variants thereof, such as AmpliTaq Gold®; (2) Klentaq-235 refers to an N-terminal deletion of the first 235 amino acids of Taq. Klentaq-235 is also known in commerce as DeltaTaq, ATaq, Klentaq, and Klentaq5; (3) Klentaq-278 refers to an N-terminal deletion of the first 278 amino acids of Taq (Klentaq-278 is also referred to as "Klentaq1" or "KT-1" or wild-type Klentaq1) and is described in claims 1-5 of U.S. Pat. No. 5,436,149; (4) Klentaq6 (abbreviated as KT-6) refers to Klentaq-278 with two amino-acid changes; (5) Klentaq7 (abbreviated as KT-7) refers to Klentaq-278 with three amino-acid changes; (6) Klentaq10 (abbreviated as KT-10) refers to Klentaq-278 with three amino acid changes; Klentaq11 (abbreviated as KT-11) refers to Klentaq-278 with four amino acid changes; Klentaq12 (abbreviated as KT-12) refers to Klentaq-278 with four amino acid changes; FL-10 refers to full-length Taq polypeptide with three amino acid changes; and FL-12 refers to full-length Taq polypeptide with four amino acid changes. These codon changes of the relevant Taq polymerase mutants are summarized in abbreviated form in Table I.

TABLE I

Codon changes in Taq DNA polymerase mutants

| SEQ ID NO:[1] | Moniker | DNA Change[2] <WT>nuc<MUT> | Codon Change(s) | Amino Acid Change(s)[2] | Pheno-type[3] |
|---|---|---|---|---|---|
| 3 | KT-6 | A2119C; (1285) | ATT to CTT; | I707L; (429) | CS |
| 4 | | A2123T; (1289) | GAG to GTG | E708V (430) | BR |
| 5 | KT-7 | G1876A; (1042) | GAG to AAG; | E626K; (348) | CS |
| 6 | | A2119C; (1285) | ATT to CTT; | I707L; (429) | CS |
| | | G2122T/A2123G (1288) (1289) | GAG to TGG | E708W (430) | BR*, FAST* |
| 19 | KT-10 | G1876A; (1042) | GAG to AAG; | E626K; (348) | CS |
| 20 | | A2119C; (1285) | ATT to CTT; | I707L; (429) | CS |
| | | G2122A (1288) | GAG to AAG | E708K (430) | BR |
| 21 | KT-11 | G1876A; (1042) | GAG to AAG; | E626K; (348) | CS |
| 22 | | G1945A; (1111) | GTC to ATC; | V649I; (371); | FAST |
| | | A2119C; (1285) | ATT to CTT; | I707L; (429) | CS |
| | | G2122A/A2123C (1288) (1289) | GAG to TCG | E708S (430) | FAST |
| 23 | KT-12 | T1826C; (992) | CTG to CCG; | L609P; (331) | BR*, FAST* |
| 24 | | G1876A; (1042) | GAG to AAG; | E626K; (348) | CS |
| | | A2119C; (1285) | ATT to CTT; | I707L; (429) | CS |
| | | G2122T/A2123T (1288) (1289) | GAG to TTG | E708L (430) | BR*, FAST* |
| 27 | FL-10 | G1876A; | GAG to AAG; | E626K; | CS |
| 28 | | A2119C; | ATT to CTT; | I707L; | CS |
| | | G2122A | GAG to AAG | E708K | BR |
| 29 | FL-12 | T1826C; | CTG to CCG; | L609P; | BR*, FAST* |
| 30 | | G1876A; | GAG to AAG; | E626K; | CS |
| | | A2119C; | ATT to CTT; | I707L; | CS |
| | | G2122T/A2123T | GAG to TTG | E708L | BR*, FAST* |

[1]Odd- and even-numbered SEQ ID NOs refer to nucleic acid and polypeptide sequences, respectively, as illustrated in the Sequence Listing.
[2]Wild-type ("WT") base of top (codon) strand on the left, mutant ("MUT") base on the right, of numerical positions of changes ("nuc") which numbers are in reference to the full-length Taq DNA polymerase encoding nucleic acid and polypeptide (herein SEQ ID NOs: 25 & 26, respectively; disclosed in GenBank Acc. No. J04639); parenthetical numbers refer to the corresponding Klentaq-278 sequence positions (herein SEQ ID NOs: 1 & 2, respectively; disclosed in U.S. Pat. No. 5,436,149).
[3]Phenotype that was conferred when this mutation was added to its parent; CS, cold sensitive; BR, blood-resistant; FAST, fast DNA extension.
*In the cases of KT-7, KT-12, and its respective FL-version, both BR and FAST phenotypes are present, presuming a possible double effect of these changes. Testing each mutation individually will clarify the linkage between the phenotypes.

The suffix "LA" means "Long and Accurate" and refers to a mixture of thermostable DNA polymerases, after claims 6-16 of U.S. Pat. No. 5,436,149 and Barnes (1994). Major component is usually Taq or Klentaq1. A minor component is usually an archaebacterial DNA polymerase such as Pfu polymerase, Pwu polymerase, Vent polymerase, or Deep Vent polymerase.

KlentaqLA is a mixture of 47:1::Klentaq1:Deep Vent by volume of commercially available enzymes. This mixture also may be modified to 24:1 as noted in the text. Since commercially distributed Klentaq1 is about 15-20 times more concentrated than commercially distributed Deep Vent, the true ratio, by units or protein, is approximately 15-20 times higher, i.e., 705:1 or 360:1

TaqLA is a mixture of 47:1::Taq:DeepVent, or 16:1::Taq:Pfu, or an unspecified mixture of Taq:Pfu that is commercially known as "TaqPlus."

Control sequences are DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

The phrase "a reaction vessel" refers to any container that may be used for performing a biological, biochemical, or chemical reaction. In the context of PCR assays, a reaction vessel is any suitable container that can withstand the temperatures carried out during a typical DNA amplification reaction. Preferably, a reaction vessel that used for PCR assays includes a tube fitted with a closure, wherein both the tube and the closure are made of polymeric material such as polypropylene or similar material commonly employed in the art.

The phrase "isolated nucleic acid molecule" is purified from the setting in which it is found in nature and is separated from at least one contaminant nucleic acid molecule.

The phrase "isolated polypeptide molecule" is purified from the setting in which it is found in nature and is separated from at least one contaminant polypeptide molecule.

The phrase "purified polypeptide" refers to a polypeptide molecule that has been purified to greater than 80% homogeneity by SDS-PAGE under non-reducing or reducing conditions using Coomassie blue or silver stain. Isolated polypeptides include those expressed heterologously in genetically engineered cells or expressed in vitro. Ordinarily, isolated polypeptides are prepared by at least one purification step.

DETAILED DESCRIPTION OF THE INVENTION

The present invention makes use of the discovery that Taq polymerases bearing certain N-terminal deletions are unusually resistant to whole blood, making them ideally suited for use in analytical PCR assays of nucleic acid targets from human blood. Furthermore, mutant(s) of full-length Taq DNA polymerase with even higher resistance to blood inhibitors have been developed that remain fully functional in the presence of at least about 20-25% blood or the equivalent of blood fractions. This level of blood tolerance exceeds that of the existing thermostable DNA polymerases (and even exceeds the amount of blood that can be practically or conveniently handled in the PCR analysis due to physical clumping). Moreover, mutants that display a high resistance to blood inhibitors have been identified that possess faster elongation rates. The use of these novel enzymes is expected to simplify and accelerate the performance of clinical and forensic tests as well as render such tests more sensitive and economical. Finally, the present invention provides methods for enhancing DNA amplification specificity using these polymerases with samples from whole blood. These Taq polymerase mutants and methods for their use are described below.

Identification of Klentaq mutants that are highly resistant to blood inhibition.

Klentaq1 polymerase (SEQ ID NO: 1 (nucleic acid) and SEQ ID NO:2 (polypeptide)) is an improved and more robust version of the Taq polymerase that bears an N-terminal deletion of 278 amino acids from the full-length (832 amino acids) enzyme. Klentaq1 displays higher fidelity and greater thermostability than Taq. Klentaq1 is also inhibited to a lesser extent than Taq when the polymerase is used in PCR assays carried out in the presence of blood products. For example, the purified Klentaq1 enzyme easily amplifies a nucleic acid target in the presence of about 5% whole blood in reaction mixture (vol/vol). This was a highly unexpected result, as the full-length Taq enzyme is completely inhibited in a blood concentration range of about 0.004% to about 0.2% whole blood in the reaction mixture (vol/vol). No correlation between the N-terminal deletion of Taq, which generates Klentaq1, and the blood resistance feature of the enzyme has been reported.

Several mutant Klentaq clones were analyzed by PCR assays for their ability to tolerate whole blood. About 40 mutagenized, yet PCR-functional Klentaq clones were constructed and tested in PCR assay mixtures containing about 10% whole human blood (vol/vol). These 40 clones are cold sensitive or are mutants of clones whose enzyme product exhibited the cold sensitive phenotype. The cold sensitivity of the additional mutant clones has not yet been determined. Remarkably, two mutants of this small collection, KT-6 (SEQ ID NO: 3 (nucleic acid); SEQ ID NO: 4 (polypeptide)) and KT-7 (SEQ ID: 5 (nucleic acid); SEQ ID NO:6 (polypeptide)), clearly outperformed the rest of the clones and the wild-type Klentaq1 protein under these conditions (FIG. 1).

Figure 2A:
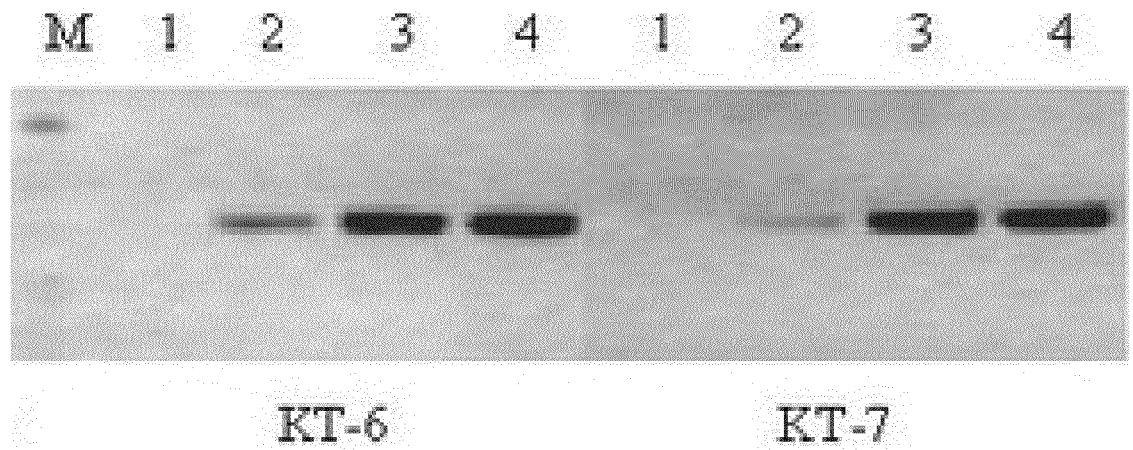
FIG. 2A depicts results of PCR amplification of a 0.32 kbp endogenous target DNA directly from whole blood with two mutant forms of Klentaq (KT-6 and KT-7) in the presence of increasing amounts of whole human blood (lane 1: 0%; lane 2: 5%; lane 3: 10%; lane 4: 15%).
Figure 2B:
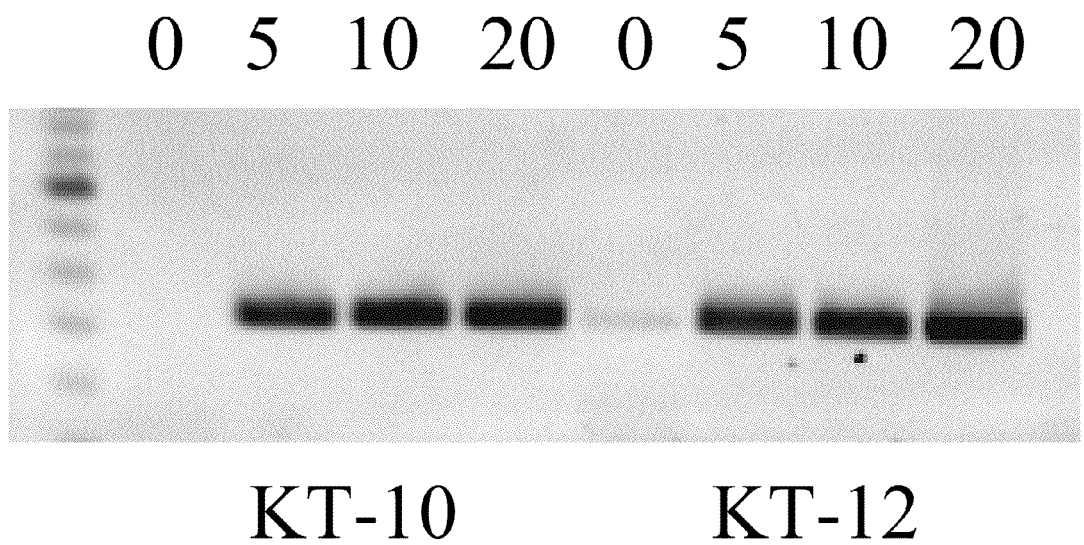
FIG. 2B depicts results of PCR assays directed toward the amplification of a 0.32 kbp endogenous human Dystrophin gene fragment in the presence of the indicated percentages of whole blood (vol/vol) in homogeneous PCR assay solutions with two mutant forms of Klentaq (KT-10 and KT-12), as shown above the figure.
Figure 2C:
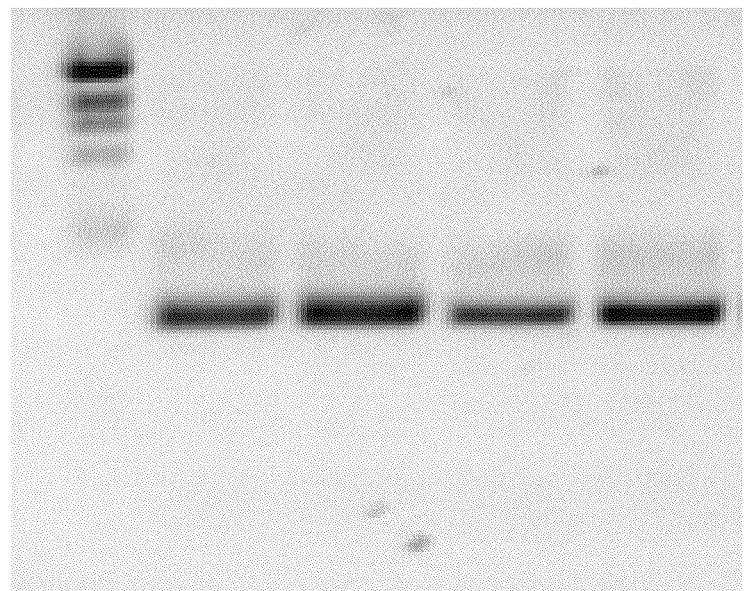
FIG. 2C depicts results of PCR assays directed toward amplification of a 1.1 kbp endogenous CCR5 gene fragment in the presence of the indicated percentages of whole blood (vol/vol) in homogeneous PCR assay solutions with two mutant forms of Klentaq (KT-10 and KT-12), as shown above the figure.

These results were confirmed by performing PCR assays in the presence of increasing amounts of whole blood. As shown in FIG. 2A, clones KT-6 and KT-7 remained functionally active in the presence of whole blood, being able to amplify an endogenous gene target directly from blood cells present in reactions containing about 15% whole human blood (vol/vol) without any DNA purification step. The presence of as little as 1% whole blood (vol/vol) in PCR assays was inhibitory for Taq (Roche) (see Example 4). Two additional mutant forms of Klentaq-278, clones KT-10 (SEQ ID NO:19 (nucleic acid) and SEQ ID NO:20 (polypeptide)) and KT-12 (SEQ ID NO:23 (nucleic acid) and SEQ ID NO:24 (polypeptide)) also displayed the ability to amplify endogenous gene targets from whole blood samples (FIGS. 2B and 2C).

The foregoing results reveal that whole blood may be used directly in screening assays to identify mutants of Klentaq-278 that are even more resistant to blood. The present invention is drawn in part to mutant forms of the Klentaq-278 DNA polymerase that display activity in PCR assays containing from about 5% whole blood to about 25% whole blood in the reaction mixture (vol/vol). More preferably, the invention is drawn to mutant forms of the Klentaq DNA polymerase that display amplification activity in PCR assays containing from about 5% whole blood to about 20% whole blood in the reaction mixture (vol/vol), including 6%, 7%, 8%, 9%, 10%, 11%, 12%, 13%, 14%, 15%, 16%, 17%, 18%, and 19% whole blood in the reaction mixture (vol/vol).

Derivation of full-length Taq mutants that are highly resistant to blood inhibition.

Figure 3A:
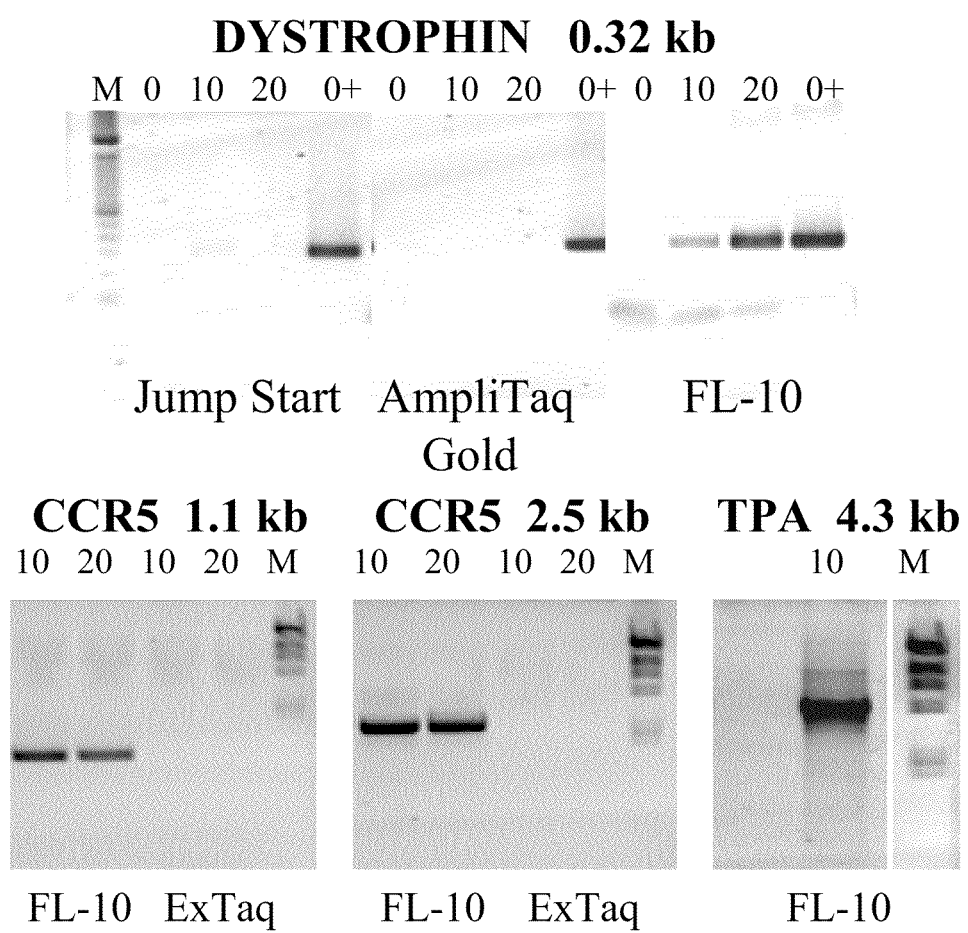
FIG. 3A depicts results of PCR assays directed toward the amplification of a 0.32 kbp fragment of the endogenous human Dystrophin gene, 1.1 kbp and 2.5 kbp fragments of the endogenous human CCR5 gene, or a 4.3 kbp endogenous human Tissue Plasminogen Activator (TPA) gene fragment in the presence of the indicated amounts of whole blood (vol/vol) (as shown above the figure) in homogeneous PCR assay solutions using a blood-resistant mutant form of full-length Taq DNA polymerase (FL-10) in comparison to blood-inactive commercial Taq enzymes (JumpStart™ Taq (Sigma), AmpliTaq Gold® (Applied Biosystems) and Ex Taq (Takara)) (lanes denoted by "0" are PCR assays conducted in the absence of blood and lanes indicated by "0+" refer to PCR assays conducted in the presence of 10 ng of human DNA).

Because the mutant forms of Klentaq-278 were more robust polymerases in whole blood PCR assays than Klentaq-278, we considered it likely that the additional amino acid changes within the structure of this truncated Taq polypeptide might confer similar blood-resistant activities when incorporated into the full-length Taq enzyme. To test this hypothesis, the region of the KT-10 gene (SEQ ID NO:19) that contains the relevant codon substitutions was re-introduced into the background of a wild-type full-length Taq (SEQ ID NO: 25 (nucleic acid) and SEQ ID NO:26 (polypeptide)) using standard recombinant DNA methods to yield the resultant mutant Taq gene, termed FL-10 (SEQ ID NO:27 (nucleic acid) and SEQ ID NO:28 (polypeptide)). The resultant polypeptide was expressed and tested in conjunction with other commercially available Taq polymerases in homogenous PCR assay solutions containing varying amounts of whole blood (0%, 10%, or 20% (vol/vol)). As is shown in FIG. 3A, FL-10 displays remarkably robust, blood-resistant, DNA amplification activity in comparison with JumpStart™ Taq, AmpliTaq Gold®, or Ex Taq™.

Figure 3B:
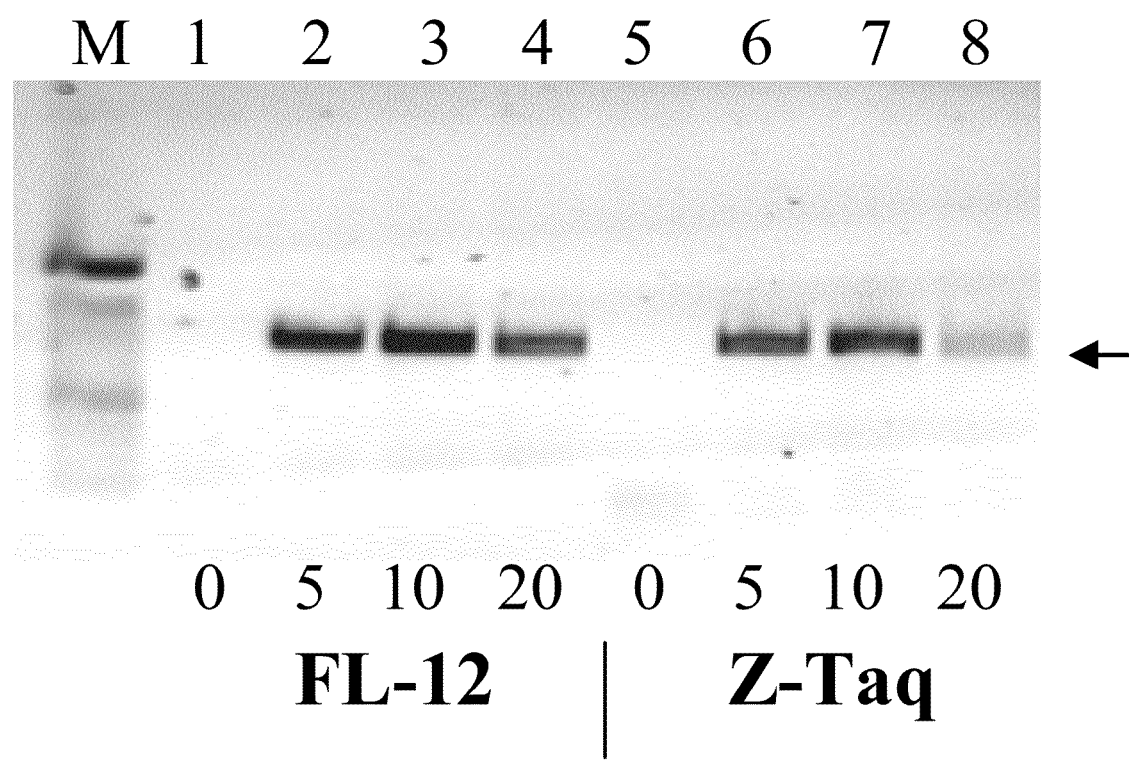
FIG. 3B depicts results of DNA amplification of a 1.1 kbp endogenous CCR5 human gene fragment (indicated by the arrow) in reactions of homogeneous PCR assay solutions containing whole blood at the indicated percentages (vol/vol) (as shown below the figure) using FL-12 and Z-TAQ™ (Takara) Taq DNA polymerases.

Similar to that found for FL-10, another mutant form of full-length Taq DNA polymerase was identified that displayed high blood-resistant DNA amplification activity. This mutant was derived by cloning the region of the KT-12 (SEQ ID NO:23) that contains the relevant codon substitutions that impart blood-resistant DNA amplification activity to the KT-12 polymerase (SEQ ID NO:24) into the background of the wild-type full-length Taq (SEQ ID NO:25) using standard recombinant DNA methods to yield the resultant mutant Taq polymerase, termed FL-12 (SEQ ID NO:29 (nucleic acid) and SEQ ID NO:30 (polypeptide)). This full-length Taq polymerase mutant displayed blood-resistant DNA amplification activity that mirrors the activity observed for the KT-12 polymerase mutant (SEQ ID NO:24) (FIG. 3B). These findings provide evidence that the region of any Klentaq-278 mutant that encodes blood-resistant DNA amplification activity will impart similar properties to the full-length Taq DNA polymerase when re-introduced into the context of the wild-type gene background.

Although both FL-10 and FL-12 Taq polymerases displayed high blood-resistant DNA amplification activity, only the FL-12 Taq polymerase displays both faster-elongating activity and high blood-resistant activity. Because these two properties are discrete attributes, we tested whether faster-elongating activity correlated with high blood-resistant activity. As described herein, Z-TAQ™ (Takara) is a proprietary form of the full-length Taq DNA polymerase that displays 5-fold faster elongation rates relative to Taq DNA polymerase. The nature of the alteration of Z-TAQ™ that is responsible for its enhanced elongation activity is unknown in the art, owing to the fact that the manufacturer of the enzyme regards Z-TAQ™ as a proprietary product. For this experiment, FL-12 Taq and Z-TAQ™ were evaluated for their respective blood-resistant DNA amplification activities. As shown in FIG. 3B, both FL-12 and Z-TAQ™ displayed blood-resistant DNA amplification activity in homogeneous PCR assay solutions, albeit the FL-12 enzyme was more robust than Z-TAQ™ in reactions containing significant amounts of whole blood (20% (vol/vol)).

One functional characteristic that distinguishes the aforementioned FL mutants (i.e., FL-10 and FL-12) from Z-TAQ™ is that the FL mutants display a cold sensitive phenotype whereas Z-TAQ™ does not. One additional functional attribute that distinguishes the aforementioned FL mutants from Z-TAQ™ is that the FL mutants are capable of carrying out DNA amplifications under hot start conditions whereas the Z-TAQ™ polymerase lacks this capability. Thus, whatever chemical or genetic attribute that endows Z-TAQ™ with its unusually high activity in whole blood PCR assays, it is not the identical modifications that render the FL mutants blood-resistant. For the purposes of this disclosure, blood-resistant DNA polymerases are defined to have three attributes: (1) display a cold sensitive phenotype in PCR assays relative to the wild-type Taq DNA polymerase; (2) display DNA amplification activity under hot start PCR conditions; and (3) display DNA amplification activity in PCR assays containing whole blood in the range from about 3% to about 25% (vol/vol).

The foregoing results reveal that whole blood may be used directly in screening assays to identify mutants of Klentaq-278 that are even more resistant to blood and that the methods are readily extendable to identifying mutants of full-length Taq that display blood-resistant DNA amplification activity. The present invention is drawn in part to mutant forms of the full-length Taq DNA polymerase that display activity in PCR assays containing from about 5% whole blood to about 25% whole blood in the reaction mixture (vol/vol). More preferably, the invention is drawn to mutant forms of the full-length Taq DNA polymerase that display amplification activity in PCR assays containing from about 5% whole blood to about 20% whole blood in the reaction mixture (vol/vol), including 6%, 7%, 8%, 9%, 10%, 11%, 12%, 13%, 14%, 15%, 16%, 17%, 18%, and 19% whole blood in the reaction mixture (vol/vol).

The presently preferred procedure for identifying blood-resistant Taq DNA polymerases is to perform two screening operations on a collection of mutants: (1) identifying those mutants that display a cold sensitive phenotype in modified PCR assays; followed by (2) characterizing the subset of cold sensitive Taq DNA polymerase mutants for DNA amplification activity in whole blood PCR assays. Even more preferably, one may initially identify blood-resistant polymerases using an adaptation of a selection procedure termed compartmentalized self-replication (25, 26) for obtaining DNA polymerase mutants with a predetermined activity. As illustrated in the Prophetic Example, one would initially select the Taq DNA polymerase mutant for its blood-resistant activity, followed secondarily by a screening procedure to characterize its cold sensitive phenotype (e.g., DNA amplification activity under hot start PCR conditions). All mutants that are blood-resistant and display a cold sensitive phenotype would comprise members of the group of blood-resistant polymerases as defined herein.

Identification of Klentaq and Taq mutants with faster DNA elongation rates

"Rapid" thermostable DNA polymerase mutants have been discovered that display a faster DNA elongation rate than found for the wild-type Klentaq-278 polymerase. By lowering the DNA extension times during PCR, certain PCR conditions have been determined where the elongation step in the cycle becomes limiting for successful amplification by the wild-type Klentaq-278 enzyme. In the case of using the Klentaq-278 gene as a target (1.65 kb long), the minimum extension time required was about 1 minute. For example, the Klentaq-278 polymerase did not possess amplification activity in PCR assays performed under conditions that employ extension times of 50 seconds. Similar results were obtained with Taq enzyme.

Figure 4A:
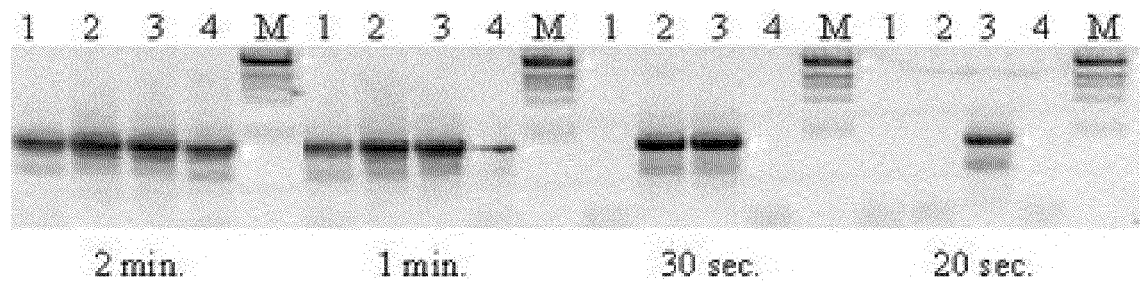
FIG. 4A depicts results of PCR amplification of a 1.65 kbp target DNA as a function of elongation time for reactions containing Klentaq1 polymerase (lane 1), two mutant Klentaq polymerases (KT-6 (lane 2) and KT-7 (lane 3)), and another commercially available Taq polymerase (lane 4). The extension times are indicated below the panel.
Figure 4B:
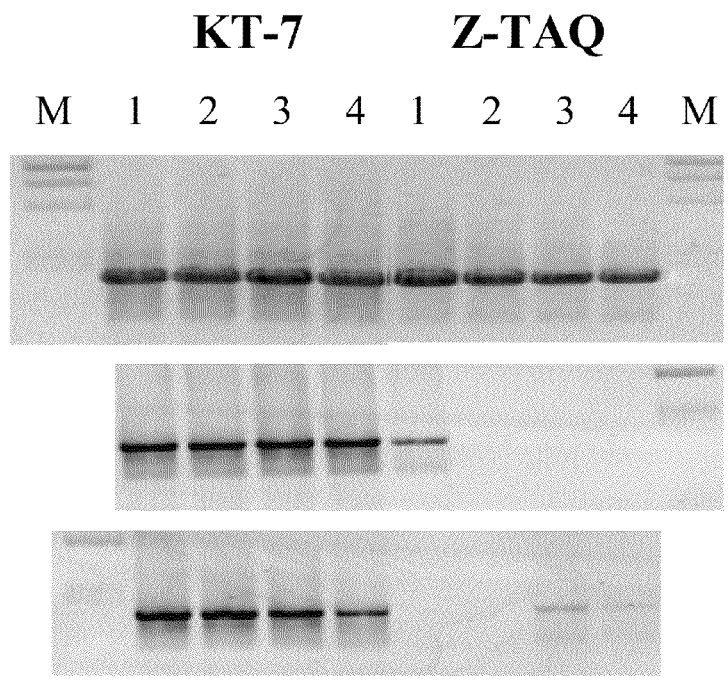
FIG. 4B depicts results of PCR amplification of a 1.65 kbp target DNA as a function of exogenous template concentration and elongation time for reactions containing a mutant Klentaq polymerase (KT-7) and a DNA polymerase that possesses the highest prior art elongation rates (Z-TAQ™). The added nucleic acid target amounts were as follows: 0.5 ng (lane 1); 0.25 ng (lane 2); 0.125 ng (lane 3); and 0.06 ng (lane 4). The extension times were as follows: 60 sec (upper panel); 15 sec (central panel); and 12 sec (lower panel).
Figure 4C:
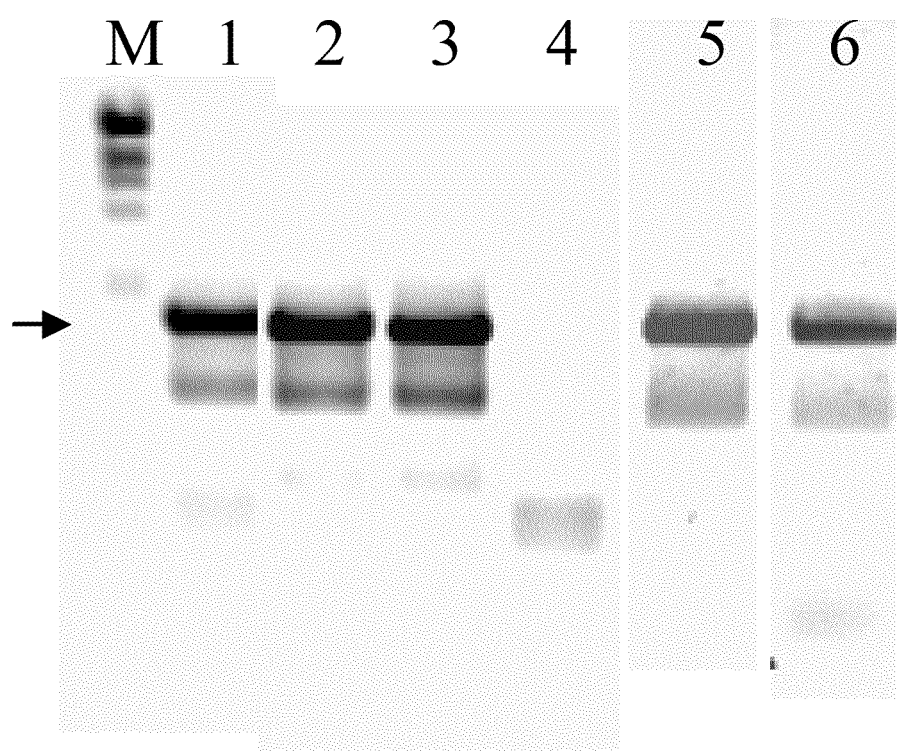
FIG. 4C depicts results of PCR amplification of a 1.65 kbp target DNA (denoted by arrow) using either mutant Klentaq DNA polymerases KT-7 (lane 1), KT-11 (lane 2), or KT-12 (lane 3), the wild-type Klentaq DNA polymerase (lane 4), the mutant full-length Taq DNA polymerase FL-12 (lane 5), or Z-TAQ™ (Takara; lane 6) performed with PCR cycles having extension steps reduced to 30 sec.

About 40 functional mutant Klentaq clones were evaluated as a function of elongation rate. A 30 sec extension time was initially employed in the PCR assays, which reflect conditions that were found ineffective for the wild-type Klentaq and AmpliTaq Gold®. Interestingly, the mutants KT-6 (SEQ ID NO:4) and KT-7 (SEQ ID NO:6) were able to efficiently amplify the target with this shorter extension time (FIG. 4). This feature of the two mutant enzymes was confirmed in further tests, wherein one of them (clone KT-7 (SEQ ID NO:6)) yielded amplification products with a 20 sec extension time (FIG. 4A). This enzyme feature was characterized further and yielded good amplification products even with 15 and 12 sec extension times (FIG. 4B). Remarkably, the selected mutant completely outperformed the Z-TAQ™ (Takara) at these low extension times (FIG. 4B, central and lower panels). Similar results were obtained with two additional mutant forms of Klentaq-278, clone KT-11 (SEQ ID NO:21 (nucleic acid) and SEQ ID NO:22 (polypeptide)) and clone KT-12 (SEQ ID NO:23 (nucleic acid) and SEQ ID NO:24 (polypeptide)) (FIG. 4C). This is noteworthy because Z-TAQ™, a proprietary Taq enzyme, is one of the fastest DNA elongating PCR enzymes that is commercially available.

Because some of the mutant forms of Klentaq-278 were faster-elongating polymerases than observed for Klentaq-278, we considered it likely that the additional amino acid changes within the structure of this truncated polypeptide might confer similar faster elongating activities when incorporated into the full-length Taq enzyme. To test this hypothesis, the region of KT-12 gene (SEQ ID NO:23) that contains the relevant codon substitutions was re-introduced into the background of a wild-type full-length Taq (SEQ ID NO:25 (nucleic acid) and SEQ ID NO:26 (polypeptide)) using standard recombinant DNA methods to yield the resultant mutant Taq gene, termed FL-12 (SEQ ID NO:29 (nucleic acid) and SEQ ID NO:30 (polypeptide)). The resultant polypeptide was expressed and tested in conjunction with other commercially available Taq polymerases in homogenous PCR assay solutions using PCR conditions wherein the extension time was reduced to 30 sec. As is shown in FIG. 4C, FL-12 displays remarkably robust, faster-elongating, DNA amplification activity in comparison to Z-TAQ™.

These results demonstrate that the elongation speed of the Klentaq DNA polymerase and the full-length Taq DNA polymerase can be improved by mutagenesis. The present invention is drawn in part to mutant forms of the Klentaq and full-length Taq DNA polymerases that display increased elongation rate in PCR assays under conditions where the respective enzymes fail to display successful amplification activity. Preferably, the invention is drawn to mutant forms of the Klentaq-278 and full-length Taq DNA polymerases that display amplification activity in PCR assays under conditions where the elongation step is time-limiting for the reaction with the wild-type Klentaq-278 polymerase. Even more preferably, the invention is drawn to mutant forms of Klentaq-278 and full-length Taq DNA polymerases that display amplification activity under PCR conditions disclosed herein and having extension times in the range from about 12 sec to about 50 sec, including 15 sec, 18 sec, 20 sec, 22 sec, 24 sec, 25 sec, 26 sec, 28 sec, 30 sec, 32 sec, 34 sec, 36 sec, 38 sec, 40 sec, 42 sec, 44 sec, 45 sec, 46 sec, and 48 sec.

Heavy hot start PCR procedures and applications to whole blood PCR

The new protocol described here uses no wax or antibodies, and requires no manipulations once the thermal cycling program has commenced. This protocol uses two aqueous layers at the time of setup of the PCR assay. The lower layer, which represents about 1/10 to about 1/4 of the final volume, includes the dNTPs and magnesium(II) that is required for the reaction. The upper layer contains the polymerase enzyme, the primers, and the nucleic acid target. Both layers contain equivalent concentrations of other buffer components at the concentrations required for amplification. The lower layer also contains a constituent to make it heavy, such as about 10-20% (wt/vol) sucrose, sorbitol or DMSO (or a suitable combination of similar reagents compatible with PCR up to about 10-20% (wt/vol)).

Optionally, other components that impart greater density to the lower layer may substitute for or supplement the items described above. For instance, Baskaran and co-workers have demonstrated that 1.4 M betaine, 5% DMSO is good for PCR assays involving nucleic acid targets possessing high GC content (36). These results suggest that inclusion of 2.8 M betaine, 10% DMSO is feasible as the heavy start component of the lower layer containing the $MgCl_2$ and the dNTPs. Optionally and routinely, color in the form of 0.05% cresol red is also included in the lower, heavy layer.

In reactions that include whole blood, the addition of components that impart greater density to the lower layer and a color agent are not required. These features are superfluous because whole blood imparts a density to the lower layer that approximates that of the aforementioned heavy layer components and because the hemoglobin of blood provides color. In reactions containing whole blood, the template is included in the heavy layer, and all other components of the reaction are in the upper layer. The range of volumes appropriate to the use of whole blood in the heavy layer comprises 1% to 25%.

Some adverse components of blood attack various components of the PCR reaction, such as the enzyme or the primers, yet the adverse components may be heat labile. Thus, the addition of the blood carefully as an unmixed underlay allows it to be added without significant contact with the putatively sensitive PCR reaction components. Upon heating to normal PCR thermal cycling temperatures of 90-95° C., many of the blood components appeared denatured and aggregated in place, were visible as brown after the cycling, and either did not mix with the PCR components before being inactivated by the heat, or never did mix appreciably with the PCR reaction components. Nevertheless, the genomic DNA template, and presumably other target templates such as viral and other microbial genomes, become timely available to the amplification reaction by convective mixing.

This principal of segregating heat labile inhibitors during reaction setup may have application to other situations of complex or environmental samples that do not involve blood.

The order of addition of the DNA polymerase cocktail and the whole blood sample to the PCR reaction vessel is not the critical aspect to the heavy hot start PCR procedure. Rather, the important aspect to the set-up of the heavy hot start PCR reaction is the careful addition of the DNA polymerase cocktail and the lower, heavier solution (e.g., a whole blood sample) to the PCR reaction vessel so as to avoid as little mixing of the individual layers of solutions as possible before thermal cycling begins. Thus, the lower, heavier solution can be initially added to the PCR reaction vessel, followed by the careful addition of the DNA polymerase cocktail as an overlayer. More preferably, however, the DNA polymerase cocktail is initially added to the PCR reaction vessel, followed by the careful addition of the lower, heavy solution to the PCR reaction vessel as an underlayer.

Figure 5A:
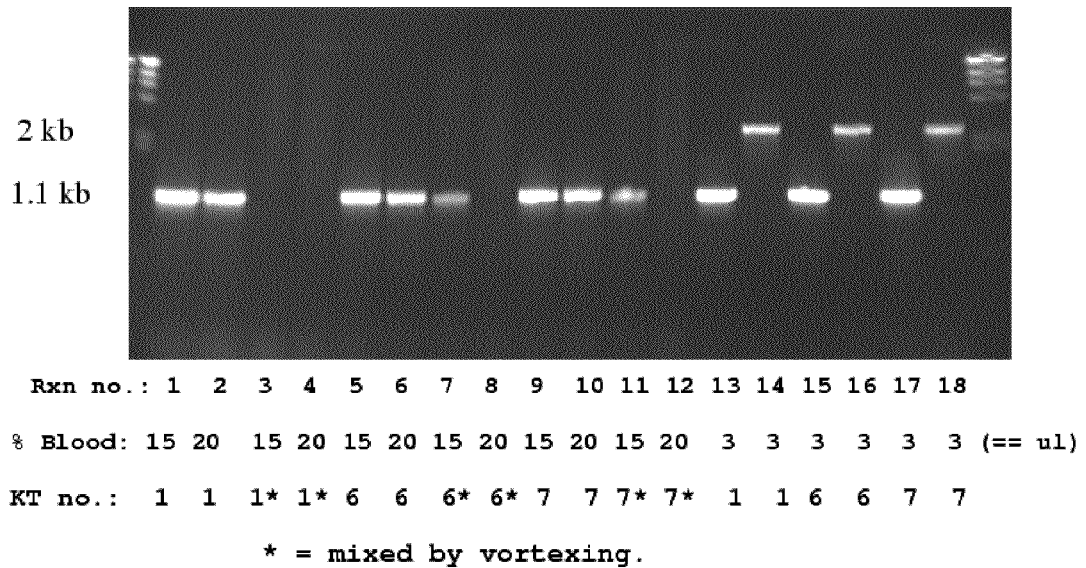
FIG. 5A illustrates the results of heavy hot start PCR assays (100 μl reaction volumes) conducted with KT-1 (SEQ ID NO:2), KT-6 (SEQ ID NO:4) and KT-7 (SEQ ID NO:6) in the presence of whole blood and under different conditions of pre-treatment of the reaction samples prior to initiating the thermal cycling program. The asterisks indicate those reaction vessels wherein the heavy and light volume component layers were premixed by vortexing, i.e., reactions that a contain homogeneous PCR assay solution and that were not subjected to a heavy hot start procedure as described herein. Lanes 1-13, 15 and 17 are PCR assays directed toward the amplification of a 1.1 kbp target from the human CCR5 gene whereas lanes 14, 16, and 18 are PCR assays directed toward the amplification of a 2.5 kbp target from the human CCR5 gene.
Figure 5B:
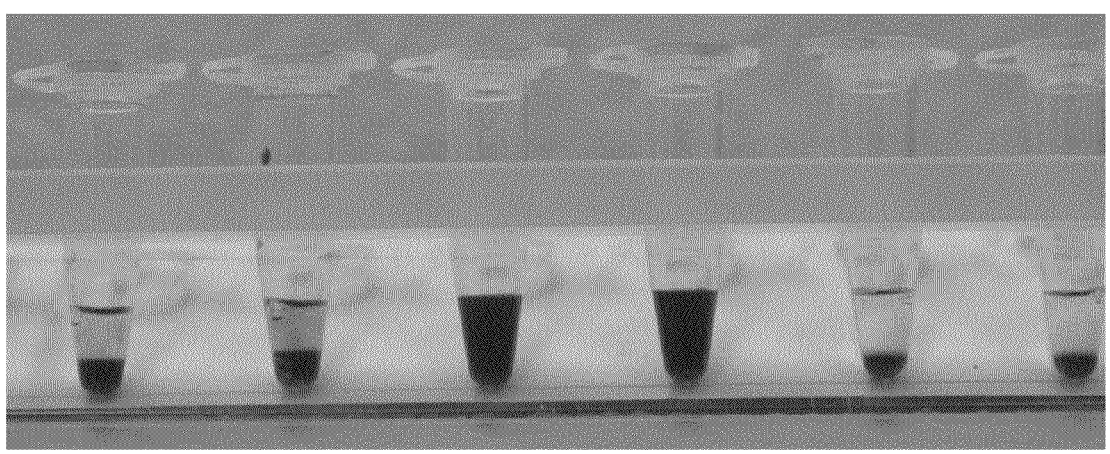
FIG. 5B illustrates an example of PCR assay tubes from reaction mixtures 9-14 of FIG. 5A that were not mixed prior to initiating the thermal cycling reaction (heavy hot start reactions; reaction nos. 9, 10, 13, and 14) or mixed by vortexing briefly prior to initiating the thermal cycling reaction (non-heavy hot start reactions; reaction nos. 11 and 12)

In the preferred embodiment, mixing of the layers occurs by diffusion and/or convection after the thermal cycler has warmed and cooled the reaction to begin the PCR process. Layered reaction tubes containing whole blood that are experimentally premixed by vortex treatment are variably unable to support PCR amplification activity, depending on the resistance of the reaction components, and the most sensitive component was discovered to be the DNA polymerase enzyme (FIG. 5A). FIG. 5B illustrates an example of PCR assay tubes that contain discrete layers prior to reaction and the mixing of the layers during reaction.

It is well understood to one of ordinary skill in the art that the combinations of components in the separate layers may be formulated in a variety of permutations. The only criteria that must be met in the present invention is that the polymerase is separated from at least one component essential to the amplification reaction (e.g., the primers, and/or the template, and/or $Mg^{2+}$), that the lower layer contains a component that imparts greater density to the solution, and that the mixing of the two layers results in reconstitution of the PCR assay conditions to permit amplification activity.

Because the inclusion of heavy reagents, such as sucrose, sorbitol or DMSO will decrease slightly the melting temperature of the nucleic acid target, the denaturation step of the PCR cycle may have to be reduced by about 1-2° C. to compensate for this effect.

Mutant forms of Taq DNA polymerase include full-length Taq DNA polymerases that contain at least one amino acid change relative to the wild-type polypeptide (SEQ ID NO:26) encoded by the nucleic acid (SEQ ID NO:25) that are illustrated in the Sequence Listing. Examples of such mutant forms of Taq DNA polymerase include FL-10 (SEQ ID NO:28) and FL-12 (SEQ ID NO:30). Additional mutant forms of Taq DNA polymerase used in the invention include truncation mutants, such as Klentaq-278 that comprises the amino acid sequence (SEQ ID NO:2) encoded by the nucleic acid (SEQ ID NO:1) whose sequences are illustrated in the Sequence Listing, or other codons that encode those amino acids, or those amino acids with a few extra codons on the amino terminus thereof. The invention also uses a mutant or variant gene encoding full-length Taq or Klentaq-278, any of whose bases may be changed from the corresponding base shown in Tables 1-6 and 8-19 while still encoding a protein that maintains the activities and physiological functions of full-length Taq or of Klentaq-278, or a slightly longer or shorter version of Klentaq-278 at the N-terminus. Further included are nucleic acids whose sequences are complementary to those just described, including complementary nucleic acid fragments. Additionally, nucleic acids or nucleic acid fragments, or complements thereto, whose structures include chemical modifications, are also included. Such modifications include, by way of nonlimiting example, modified bases, and nucleic acids whose sugar phosphate backbones are modified or derivatized. In the mutant or variant nucleic acids, and their complements, up to 20% or more of the bases may be so changed.

The invention also includes the use of polypeptides and nucleotides having 80-100% sequence identity to SEQ ID NOS:1-6 and 19-30, including 81, 82, 83, 84, 85, 86, 87, 88, 89, 90, 91, 92, 93, 94, 95, 96, 97, 98, and 99% sequence identity to SEQ ID NOS:1-6 and 19-30, as well as nucleotides encoding any of these polypeptides, and complements of any of these nucleotides. In the case of Klentaq1 (SEQ ID NO:1), the invention includes mutant forms that contain at least one codon change in the open reading frame of Klentaq1 (SEQ ID NO:2). In the case of Taq DNA polymerase (SEQ ID NO:25), the invention includes mutant forms that contain at least one codon change in the open reading frame of Taq DNA polymerase (SEQ ID NO:26).

Percentage Sequence Identity

"Percent (%) nucleic acid sequence identity" with respect to Klentaq-278-encoding nucleic acid sequences identified herein is defined as the percentage of nucleotides in a candidate sequence that are identical with the nucleotides in the Klentaq-278 sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. The same methods and principles apply to ascertain "percent (%) nucleic sequence identity with respect to Taq DNA polymerase-encoding nucleic acid sequences in a candidate nucleic acid sequence when the two sequences are aligned.

When nucleotide sequences are aligned, the percent (%) nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

% nucleic acid sequence identity=$W/Z*100$ where

W is the number of nucleotides scored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

"Percent (%) amino acid sequence identity" is defined as the percentage of amino acid residues that are identical with amino acid residues in the disclosed Klentaq-278 DNA polymerase polypeptide sequences in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full-length of the sequences being compared. The same methods and principles apply to ascertain "percent (%) amino acid sequence identity with respect to Taq DNA polymerase-encoding polypeptide sequences in candidate sequences when the two sequences are aligned.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y*100$ where

X is the number of amino acid residues scored as identical matches by the sequence alignment program's or algorithm's alignment of A and B; and Y is the total number of amino acid residues in B.

If the length of amino acid sequence A is not equal to the length of amino acid sequence B, the % amino acid sequence identity of A to B will not equal the % amino acid sequence identity of B to A.

A nucleic acid molecule used in the invention, e.g. a nucleic acid molecule having the nucleotide sequence of SEQ ID NOS:1, 3, 5, 19, 21, 23, 25, 27, or 29 or a complement of this aforementioned nucleotide sequence, can be isolated using standard molecular biology techniques and the provided sequence information. Using all or a portion of the nucleic acid sequence of SEQ ID NOS:1, 3, 5, 19, 21, 23, 25, 27, or 29 as a hybridization probe, Klentaq-278 or Taq gene molecules can be isolated using standard hybridization and cloning techniques (29, 30).

PCR amplification techniques can be used to amplify Klentaq-278 or Taq encoding DNA using Thermus aquaticus genomic DNA as a template and appropriate oligonucleotide primers. Furthermore, oligonucleotides corresponding to Klentaq-278 or Taq gene sequences can be prepared by standard synthetic techniques, e.g., an automated DNA synthesizer.

Klentaq-278 is the subject of U.S. Pat. No. 5,436,149 (31), which is incorporated herein by reference.

Klentaq-235 is the subject of U.S. Pat. No. 5,616,494 (32), which is incorporated herein by reference.

Medical Applications

The applications of the present invention include diagnostic evaluations of whole blood samples for the presence and status of genetic disorders (e.g., cancer, blood disorders, diabetes, etc.) and diseases caused by blood borne microbial agents (e.g. viruses, bacteria, fungi, etc.); tissue-typing using polymorphisms, and forensic research. One of ordinary skill would recognize the utilities of blood-resistant polymerases and high elongating polymerases of the present invention toward advancing the application of PCR to whole blood samples directed to these objectives.

Kits

The present invention also contemplates kits that may be employed in the clinical setting or in the field for permitting a simplified set of reagents for rapid PCR analysis of whole blood samples using the blood-resistant polymerases and high elongating polymerases of the present invention. Kits would typically include suitable oligonucleotide primers, PCR reaction buffer components, control solutions, and a suitable DNA polymerase, as well as instructions for the kit's use. Preferred DNA polymerases include the disclosed blood-resistant polymerases as defined herein (e.g., KT mutants that are blood-resistant and display a cold sensitive phenotype) as well as the Z-TAQ™enzyme and the KT-1 enzyme (each of which displayed moderate blood resistance, but not cold sensitive).

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Screening of Mutagenized Klentaq Clones for Blood-Resistant Mutant Enzyme Activity In order to functionally characterize new mutants, it is desirable to produce highly-purified enzyme from expression systems. The procedure, which included PEI treatment, BioRex-70 chromatography, and Heparin-Agarose chromatography, yielded DNA-free and nuclease-free Klentaq enzyme purified to homogeneity, as judged by a single band in Coomassie stained protein gel (23). The same purification procedure also worked very well for purification of cold sensitive Klentaq mutants (23). This procedure was readily adaptable to accommodate purification of mutant polymerases that display unusual features such as changed affinity and elution profile on a particular chromatography resin. The efficiency of each step in the purification scheme was monitored easily by a standard DNA incorporation assay.

The amplification activity of the obtained mutant enzymes were extensively evaluated in PCR amplification of various gene targets. The new enzymes were tested both in conventional and real-time PCR with SYBR green fluorescent detection. These tests included at least about 20% whole human blood (untreated, EDTA-treated, or heparinized), or blood IgG and hemoglobin fractions equivalent. Optionally, the differential sensitivities that the polymerase mutants display toward whole blood were evaluated by performing an amplification activity titration experiment with increasing incremental amounts of whole blood added to the assay mixtures from about 5% whole blood (vol/vol) to about 25% whole blood (vol/vol).

FIG. 1 illustrates the results of screening of a collection of 40 KT mutants by PCR assay with homogeneous PCR assay solutions containing 10% whole blood (vol/vol), wherein the Klentaq gene represented the target nucleic acid. The primers used in the PCR assays comprise KT1 (SEQ ID NO:11) and RevTaqH (SEQ ID NO:12), which resulted in the specific amplification of a 1.65 kbp target fragment.

FIG. 2A illustrates the results of typical PCR assays with homogeneous PCR assay solutions containing different amounts of whole blood (vol/vol) in the reaction, wherein an endogenous human gene from blood represents the target nucleic acid. The primers used in the PCR assays comprise DMDex21 f (SEQ ID NO:13) and DMDex21r (SEQ ID NO:14), which resulted in the specific amplification of a 0.32 kbp target fragment of the endogenous human Duchenne muscular dystrophy gene (Dystrophin).

In order to confirm the blood resistance feature of the Klentaq mutant enzymes, numerous exogenous and endogenous test gene targets were used. Two to three ng plasmid pWB254 DNA or human DNA were used as exogenous targets to amplify the Klentaq gene itself (1.65 kb fragment, which was obtained with primers KT1 (SEQ ID NO:11) and RevTaqH (SEQ ID NO:12)) or a 4.3 kb fragment of the human TPA gene (obtained with primers TPA forward (SEQ ID NO:17) and TPA reverse (SEQ ID NO:18)), respectively. The endogenous targets (from DNA present in the blood cells) included a 0.32 kb amplicon of the human Dystrophin gene (obtained with primers DMDex2lf (SEQ ID NO:13) and DMDex21r (SEQ ID NO:14) and 1.1 kb or 2.5 kb amplicons of the human CCR5 gene (obtained with primer pairs ccr5+lkb (SEQ ID NO:9)/CCR5-KOZ (SEQ ID NO:7) and CCR5-2kb (SEQ ID NO:8)/ccr5deltaRT (SEQ ID NO:10), respectively). Whole or EDTA-treated (4.8 mM EDTA) human blood was added at concentrations 0%-20% to the PCR cocktail prior to PCR (homogeneous PCR setup). As illustrated in FIGS. 2B and 2C, KT-10 and KT-12 mutants easily amplified the targets in at least 20% whole blood. The wild-type Taq enzyme failed under comparable conditions. The amplification signal obtained with the mutants when detecting endogenous blood genes was gene-dose–responsive.

Example 2

Full-Length Taq DNA Polymerase Mutants Display Blood-Resistant Activity

Importantly, the amino acid changes responsible for the blood-resistant phenotype of the Klentaq, were also sufficient to render the full-length Taq blood-resistant when these amino acid changes were incorporated into the full-length gene. For example, the amino acid changes of KT-10 and KT-12 mutants were incorporated into the full-length Taq gene to generate the analogous Taq-mutants FL-10 and FL-12. As shown in FIG. 3A (for FL-10) and FIG. 3B (for FL-12), both full-length Taq mutants exhibited very high resistance to blood inhibition, and successfully amplified the endogenous human Dystrophin and CCR5 genes in homogeneous PCR solutions containing 20% blood. The observed high blood resistance of these mutants reflects dramatic change in the property of the Taq enzyme, considering the fact that the wild-type Taq is typically inactivated in homogeneous PCR assay solutions containing as little as 0.1-0.5% whole blood. Various commercial Taq enzymes, including AmpliTaq Gold®, JumpStart™ Taq, and Ex Taq™ failed to detect endogenous blood genes even at the lowest blood concentrations tested. One surprising exception was the enzyme Z-TAQ™, which showed a significant blood resistance at 5% and 10% blood; however, the FL-12 polymerase mutant outperformed Z-TAQ™ when used in homogeneous PCR assay solutions containing 20% blood to amplify a 1.1 kbp fragment of the endogenous CCR5 gene with primers ccr5+lkb (SEQ ID NO:9) and CCR5-KOZ (SEQ ID NO:7)) (FIG. 3B). The molecular change in the Z-TAQ™ enzyme responsible for its blood-resistant property is unknown, as the manufacturer (Takara) maintains its composition as a proprietary secret.

Example 3

Mutagenized Klentaq Mutants with a Faster DNA Elongation Rate

The screening factor here is to simply shorten the DNA extension step of the PCR cycle beyond the point where the wild-type or prior art enzyme stops working. In the case when wild-type Klentaq amplified its own gene, the amplification efficiency was significantly lower at 60 seconds extension step (FIG. 4A, lane 1 at 1 min). Additional tests with discrete extension times showed that the Klentaq polymerase did not display amplification activity in PCR assays performed under conditions that employ an extension time of about 50 sec or less (e.g., see FIG. 4A, lane 1 at 30 sec and 20 sec). On the other hand, mutant Klentaq clone KT-7 displayed amplification activity with the same target in PCR assays under conditions having an extension step of as little as about 12 sec. (FIG. 4B, lower panel). For the evaluation of fast-elongating mutants, extension times in the PCR cycle not exceeding 20 sec per 2 kb amplicon were used. The KT mutants, KT-7 (SEQ ID NO:6), KT-11 (SEQ ID NO:21), and KT-12 (SEQ ID NO:24) were markedly faster elongating polymerases than KT-1 (SEQ ID NO:2), whereas the full-length Taq mutant, FL-12 (SEQ ID NO:30), displayed increased elongation activity relative to Z-TAQ™ (FIG. 4C). For these experiments, the PCR assays were conducted using homogeneous PCR assay solutions with KT1 (SEQ ID NO:11) and RevTaqH (SEQ ID NO:12), which resulted in the specific amplification of a 1.65 kbp target fragment from the Klentaq1 gene.

Example 4

L Hot Start Achieved by Underlay of Heavy Liquid Component can Enhance Yield of Specific Amplification Products—"Heavy Hot Start" Amplification This amplification procedure permits one to obtain an enhanced specificity and reliability from a PCR assay. The strategy is also amenable to PCR assays involving whole blood, as described below. In two preferred embodiments, two heavy hot start mixes are disclosed that differ mainly in the amounts of $Mg^{2+}$ and dNTPs present in the reaction mixture, since the optimum $Mg^{2+}$ and dNTP concentrations for Klentaq1 and KlentaqLA is higher than for Taq and TaqLA. These heavy hot start mixes can be stored for at least a month at 4° C.

10×TCA is 500 mM Tris-HCl pH 9.2, 160 mM ammonium sulfate. When the pH of the Tris-HCl stock was adjusted to pH 9.2, the pH of the aliquots was measured at a buffer concentration of 50 mM in water at room temperature. The concentration of the 1 M $MgCl_2$ stock was confirmed by determining the refractive index of the solution using a refractometer and by reference to Refractive Index-Concentration Data in a technical manual, such as THE HANDBOOK OF CHEMISTRY AND PHYSICS by Chemical Rubber Company.

The heavy mix recipe for the KlentaqLA yielded a final Mg(II) cation concentration that was 2.5 mM greater than the total concentration of the dNTP. This heavy mix recipe consists of the following components: 100 µl of 10×TCA; 100 µl of a dNTP mix consisting of 10 mM DATP, 10 mM dGTP, 10 mM dCTP, and 10 mM dTTP; 140 µl of 100 mM $MgCl_2$, 67 µl of 0.75 mM Cresol Red, 4.25 mM Tris Base, 400 µl of 50% Sucrose or Sorbitol; and 193 µl of water to 1 ml.

The heavy mix recipe for Taq or TaqLA yielded final Mg(II) cation concentration that was 0.75 mM greater than the total concentration of the dNTPs. This heavy mix recipe consists of the following components: 100 µl of 10×TCA; 94 of 100 mM $MgCl_2$, 16 µl of 100 mM dATP; 16 µl of 100 mM dGTP; 16 µl of 100 mM dCTP; 16111 of 100 mM dTTP; 67 µl of 0.75 mM Cresol Red, 4.25 mM Tris Base 400 µl of 50% Sucrose or Sorbitol; and 275 µl of water to 1 ml.

Typical reaction mixtures were assembled with the following components: 3.75 µl 10×TCA; 1.0 ng target DNA; 1.0 µl (each) 10 µl primers; 0.25 to 0.50 µl enzyme; 30.25 µl water to a final volume of 37.5 µl. This initial mixture represented the top layer. The top layer was added to the PCR assay tube, followed by the addition of oil (if desired or necessary). The PCR tube was subjected to a brief centrifugation step to resolve the aqueous and oil layers. Finally, 13.0 µl of heavy mix was added as an underlayer of the PCR tube contents without mixing. The tubes were closed and carefully carried to and installed into the thermal cycler without undue agitation. The thermal cycler was set to start with a 5 min heating step from 60° C. to 68° C. before the first heat denaturation step. A visual inspection of the tubes thereafter confirmed that the two layers had already mixed during this time.

For heavy hot start PCR assays that included whole blood in the heavy layer, the following experiment was performed. One hundred microliter reactions were assembled with the whole blood being added last. The top layer consisted of 80 µl mixtures, wherein each mixture contained 0.25 µl of polymerase selected from the group consisting of Klentaq1 (Klentaq-278), Klentaq5 (Klentaq-235), Klentaq6, Klentaq7, additional mutants, and Taq. Before the blood was added, water was added to complement the blood volume, so that at the final volume would be 100 µl even though the volume of the heavy, whole blood underlay ranged from 0.5 µl to 20. The blood was carefully added at the bottom of the tubes, underneath the 80 µl top layer. For example, in PCR assays that contained 0.5 µl of blood, 19.5 µl of water was added to the upper layer before the blood was added as an underlay at the bottom of the tube. The layers were not manually mixed before the PCR assay was performed. The primers were present at 20 pmoles each per 100 µl reaction. The buffer was KLA pH 9, the concentration of dNTPs was 100 µm each, and 1.3 M betaine was present (all concentrations as final in the 100 µL). Ten nanograms of human DNA (from Novagen) was included in the two of the no-blood reactions (the ones catalyzed by Klentaq-235 and Taq) (indicated by lanes denoted by "0+") to provide a positive control for the polymerise activity. The thermal cycling program was 3 min preheat at 60° C., 35 cycles of (71 sec at 93° C., 60 sec at 60° C., and 5 min at 68° C.).

FIG. 5A illustrates the results of heavy hot start PCR assays (100 µL reaction volumes) conducted with KT-1 (SEQ ID NO:2), KT-6 (SEQ ID NO:4) and KT-7 (SEQ ID NO:6) in the presence of whole blood and under different conditions of pre-treatment of the reaction samples prior to initiating the thermal cycling program. The asterisks indicate those reaction vessels wherein the heavy and light volume component layers were premixed by vortexing, i.e., reactions that a contain homogeneous PCR assay solution and that were not subjected to a heavy hot start procedure as described herein. Lanes 1-13, 15 and 17 are PCR assays directed toward the amplification of a 1.1 kbp target from the human CCR5 gene using ccr5+lkb (SEQ ID NO:9) and CCR5-KOZ (SEQ ID NO:7). Lanes 14, 16, and 18 are PCR assays directed toward the amplification of a 2.5 kbp target from the human CCR5 gene using CCR5-2 kb (SEQ ID NO:8) and ccr5deltaRT (SEQ ID NO:10).

Figure 6:
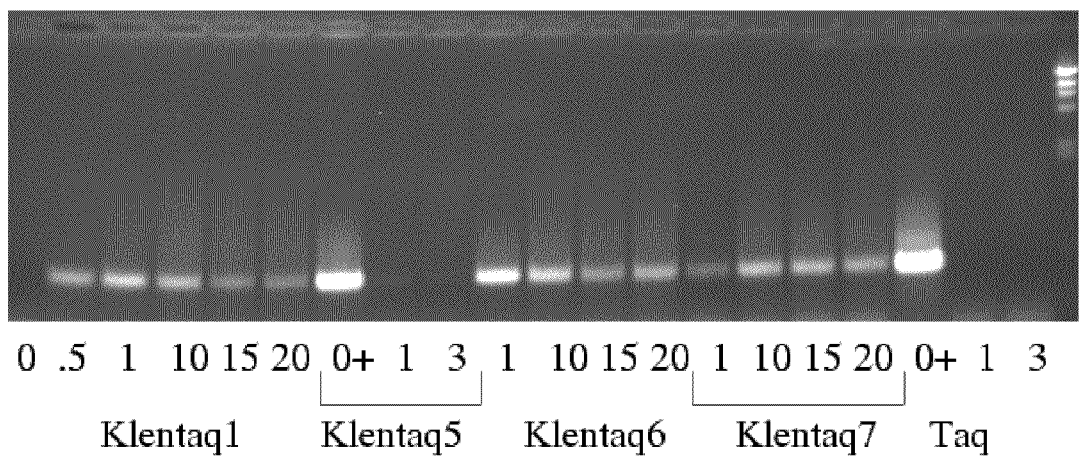
FIG. 6 depicts results of heavy hot start PCR amplification of a 0.5 kbp target from the human CCR5 gene of cells present in whole blood. The reactions were conducted in the presence of whole blood in the lower layer at the percentages indicated below each lane (vol/vol; adjusted for total volume of both layers), in the absence of whole blood (indicated by "0"), or in absence of blood and in the presence of 10 ng of human DNA (indicated by "0+").

FIG. 6 depicts the additional results of this type of experiment. The amplification activity was revealed by the specific amplification of a 0.5 kbp DNA product from the CCR5 gene endogenous to the human cells in the blood (except for the lanes indicated by "0+", which indicates the presence 10 ng of exogenous human DNA template without whole blood). KT-1 (SEQ ID NO:2), KT-6 (SEQ ID NO:4), and KT-7 (SEQ ID NO:6) displayed DNA amplification activity in reaction containing from about 1% whole blood (vol/vol) to about 20% whole blood (vol/vol) whereas Klentaq5 and Taq did not display amplification activity in reactions containing as little as about 1% whole blood (vol/vol). The primers used to generate this amplification product were CCR5-D5 (SEQ ID NO:15) and CCR5-D3 (SEQ ID NO:16).

Example 5

Whole Blood PCR Assays that Employ KT Mutant Polymerases with a Second Thermostable DNA Polymerase Having a 3'-Exonuclease Activity This example shows that long and accurate PCR works with whole blood as the source of the target template. Since long and accurate PCR (U.S. Pat. No. 5,436,149, claims 6-16) comprises the use of a mixture of DNA polymerases, this example also illustrates that the minor component of the mixture, an archaebacterial DNA polymerase which is thermostable and which exhibits 3'-exonuclease activity, is surprisingly active with whole blood.

The master PCR cocktail was assembled as follows:
200 μl 10×KLA pH 9
20 μl 10/40 (mix of 10 mM each dNTP and 40 mM MgCl2)
520 μl 5 M Betaine
40 μl primer CCR5-2 kb (SEQ ID NO:8)
40 μl primer ccr5deltaRT (SEQ ID NO:10)
1120 μl water to make 20×97 μl reaction mixture aliquots
1940 μl total cocktail volume It is worth noting that the PCR cocktail lacked target nucleic acid template and the DNA polymerase at this stage.

Enzyme dilutions were prepared on ice by mixing them with a portion of the master mix as follows: six aliquots (75 μl each) of master mix were withdrawn and added to an aliquot (0.75 μl) of enzymes KT-1 (SEQ ID NO:2), KT-6 (SEQ ID NO:4), or KT-7 (SEQ ID NO:6) each at about 30 U/μl, and the same three enzymes that have been previously mixed with 1:24 dilution volume of the archaebacterial enzyme Deep Vent, which is available commercially at 2 U/μl. These latter enzyme mixtures possessed a ratio of KT enzyme to Deep Vent enzyme of about 1:360.

Aliquots of the master mix (72 μl) were dispensed to reaction tubes, then aliquots of the appropriate enzyme dilution mix (25 μl) were dispensed into the reaction tubes to provide for a total volume of 97 μl.

Pure human DNA (Novagen), stored at a temperature of 4° C. and at a concentration of 3 ng/μl, was diluted 3-fold with standard TEN buffer (10 mM Tris pH 7.9, 10 mM NaCl, 0.1 mM EDTA) to make 1 ng/μl, and then an aliquot of this solution (3 μl) was pipetted into the aforementioned 97 μl mixture to yield the final PCR assay mastermix.

Whole blood, which is typically stored in an aliquot of 0.5 ml with 4.5 mM EDTA at −80° C., was thawed at room temperature for about 15 to 30 minutes and mixed by gentle inversion before 3 μl was pipetted underneath the aforementioned 97 μl mixture in additional PCR reaction tubes, avoiding mixing. The pipettor was set to 3.2 μl and care was exercised not eject the last small amount of blood volume (0.2 μl), so as to avoid injecting a bubble of air into the PCR assay solution and thereby disturb the heavy phase at the bottom of the tube.

Thermal cycling for the PCR amplification was carried out using a similar program as described above (2 minutes at 93° C., followed by 33 cycles of (71 seconds at 93° C., 1 minute at 60° C., 10 minutes at 68° C.). After the PCR assays were completed, aliquots of the reactions (18 μl) were mixed with 4.4 μl of blue dye mix, and analyzed by electrophoresis on a 1.4% agarose gel.

Figure 7:
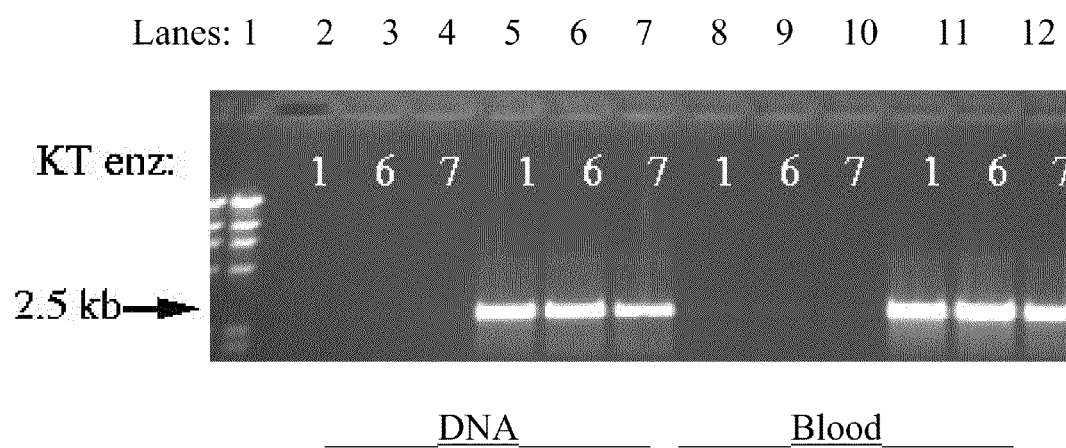
FIG. 7 depicts results of PCR assays directed toward the amplification of a 2.5 kbp target from the human CCR5 gene derived from 2 ng of genomic DNA (designated "DNA") or from 3% whole blood (vol/vol) (designated "Blood") using either KT-1 (SEQ ID NO:2), KT-6 (SEQ ID NO:4), or KT-7 (SEQ ID NO:6) in the absence of Deep Vent polymerase (lanes 1-3 and 7-9) or in the presence of Deep Vent polymerase (lanes 4-6 and 10-12), wherein the ratio of the KT enzyme to Deep Vent polymerase is about 360 to 1.

FIG. 7 illustrates that little or no PCR product of the expected size (2.5 kbp) is obtained unless an amount of Deep Vent polymerase is present to complement the major DNA polymerase Klentaq1 (SEQ ID NO:2), Klentaq6 (SEQ ID NO:4), or Klentaq7 (SEQ ID NO:6), all of which perform equally well under these conditions.

Example 6

Selection of Blood-Resistant Klentaq DNA Polymerase Mutants Using Compartmentalized Self-Replication The recently described highly effective compartmentalized self-replication (CSR) strategy for directed evolution of enzymes (25, 26) could be adapted to select for blood-resistant Klentaq mutants. The existence of blood-resistant mutant(s) of Klentaq should be evident in the library as a manifestation of detectable self-replication of the Klentaq gene in the presence of 10% blood, a concentration that is inhibitory for the wild-type Klentaq. Blood-resistant Klentaq clones could be isolated and Klentaq mutant proteins prepared according to the procedures set forth in Example 1. Individual Klentaq polymerase mutants could then subjected to screening procedures to ascertain whether each displays a cold sensitive phenotype. Those Klentaq mutants that are blood-resistant and display a cold sensitive phenotype would be expected to conform to the group of blood-resistant DNA polymerases as defined herein. The aforementioned selection/screening procedure should also be amenable to identifying full-length Taq DNA polymerase mutants that are blood-resistant DNA polymerases as defined herein.

SEQUENCE INFORMATION

The nucleic acids and polypeptides of the various DNA polymerases and the oligonucleotide primers described in this application include the sequences shown in the Sequence Listing. Table II provides the nucleic acid sequences for the specific oligonucleotide primers used in the various examples disclosed in this application.

TABLE II

| Nucleic acid sequences of oligonucleotides | | |
|---|---|---|
| SEQ ID NO.: | Name | Primer Sequence (5'→3') |
| 7 | CCR5 – KOZ | TGGAACAAGATGGATTATCAAGTGTCAAGTCAA |
| 8 | CCR5 – 2kb | AGAAGAGCTGAGACATCCGTTCCCCTACAAGAA |
| 9 | ccr5 + 1kb | AGGCTGTGTATGAAAACTAAGCCATGTGCACAA |
| 10 | ccr5deltaRT | GCAGCGGCAGGACCAGCCCCAAGATGACTATCT |

TABLE II-continued

Nucleic acid sequences of oligonucleotides

| SEQ ID NO.: | Name | Primer Sequence (5'→3') |
|---|---|---|
| 11 | KT1 | GAGCCATGGTCCTCCTCCACGAGTTCGGCCTTCTGG |
| 12 | RevTaqH | CGGTCCGAAAGCTTCTATCACTCCTTGGCGG |
| 13 | DMDex21f | GGCTGTGATAGAGGCTTGTCTATA |
| 14 | DMDex21r | CTGGCCTGCACATCAGAAAAGACT |
| 15 | CCR5 – D5 | AGGTACCTGGCTGTCGTCCATGCTGTGTTT |
| 16 | CCR5 – D3 | GATGATGGGGTTGATGCAGCAGTGCGTCAT |
| 17 | TPA forward | GGAAGTACAGCTCAGAGTTCTGCAGCACCCCTGC |
| 18 | TPA reverse | GATGCGAAACTGAGGCTGGCTGTACTGTCTC |

REFERENCES

Lantz P-G, Al-Soud W A, Knutsson R. Hahn-Hagerdal B, Radstrom P. 2000. Biotechnical use of the polymerase chain reaction for microbial analysis of biological samples, p. 87-130. In M. R. El-Gewely (ed.), BIOTECHNOLOGY ANNUAL REVIEW, vol. 5. (Elsevier Science B.V., Amsterdam, The Netherlands).

Altwegg M, Verhoef J. 1995. Amplification methods in diagnostic microbiology. J. Microbiol. Methods 23:3-138.

Al-Soud W A, Radstrom P. 2000. Effect of amplification facilitators on diagnostic PCR in the presence of blood, feces and meat. J. Clin. Microbiol. 38:4463-70.

Al-Soud A W, Jonsson L J, Radstrom P. 2000. Identification and characterization of immunoglobulin G in blood as a major inhibitor of diagnostic PCR. I Clin. Microbiol. 38:345-50.

de Franchis R, Cross N C P, Foulkes N S, Cox T M. 1988. A potent inhibitor of Taq polymerase copurifies with human genomic DNA. Nucleic Acids Res. 16:10355.

Al-Soud A W, Radstrom P. 1998. Capacity of nine thermostable DNA polymerases to mediate DNA amplification in the presence of PCR-inhibiting samples. Appl. Environ. Microbiol. 64:3748-53.

Al-Soud W A, Radstrom P. 2001. Purification ands characterization of PCR-inhibitory components in blood cells. J. Clin. Microbiol. 39:485-93.

Frackman S, Kobs G, Simpson D, Storts D. 1998. Betaine and DMSO: enhancing agents for PCR. Promega Notes 65:27.

Topal M D, Sinha N K. 1983. Products of bacteriophage T4 genes 32 and 45 improve the accuracy of DNA replication in vitro. J. Biol. Chem. 258: 12274-79.

Akane A, Matsubara K, Nakamura H, Takahashi S, Kimura K. 1994. Identification of the heme compound copurified with deoxyribonucleic acid (DNA) from bloodstains, a major inhibitor of polymerase chain reaction (PCR) amplification. J. Forensic Sci. 39:362-72.

Kreader C A. 1996. Relief of amplification inhibition in PCR with bovine serum albumin or T4 gene 32 protein. Appl. Environ. Microbiol. 62:1102-06.

Morata P, Queipo-Ortuno I, Colmenero J. 1998. Strategy for optimizing DNA amplification in a peripheral blood PCR assay used for diagnosis of human brucellosis. J. Clin. Microbiol. 36:2443-46.

Rossen L, Noskov P, Holmstrom K, Rasmussen O F. 1992. Inhibition of PCR by components of food samples, microbial diagnostic assays and DNA-extraction solution. Int. J. Food Microbiol. 17:37-45.

Izraeli S, Pfleiderer C, Lion T. 1991. Detection of gene expression by PCR amplification of RNA derived from frozen heparinized whole blood. Nucleic Acids Res. 19:6051.

Wilson I G. 1997. Inhibition and facilitation of nucleic acid amplification. Appl. Environ. Microbiol. 63:3741-51.

Al-Soud A W, Lantz P-G, Backman A, Olcen P, Radstrom P. 1998. A sample preparation method which facilitates detection of bacteria in blood cultures by the polymerase chain reaction. J. Microbiol. Methods 32:217-224.

Klein A, Barsuk R, Dagan S, Nusbaum 0, Shouval D, Galun E. 1997. Comparison of methods for extraction of nucleic acid from hemolytic serum for PCR amplification of hepatitis B virus DNA sequences. J. Clin. Microbiol. 35:1897-99.

Cattaneo C, Graig O E, James N T, Bolton H. 1997. Comparison of three DNA extraction methods on bone and blood stains up to 43 years old and amplification of three different gene sequences. J Forensic Sci. 42:1126-35.

Bourke M T, Scherczinger C A, Ladd C, Lee H C. 1999. NaOH treatment to neutralize inhibitors of Taq polymerase. J Forensic Sci. 44: 1046-50.

Kox L F, Rhienthong D, Miranda A M, Udomsantisuk N, Ellis K, van Leeuwven J, van Heusden S, Kuijper S, Kolk A H. 1994. A more reliable PCR for detection of *Mycobacterium tuberculosis* in clinical samples. J Clin. Microbiol. 32:672-80.

Kramvis A, Bukovzer S, Kew M C. 1996. Comparison of hepatitis B virus DNA extractions from serum by the QIAamp blood kit, Genereleaser, and the phenol-chloroform method. J. Clin. Microbiol. 34:2731-33.

Barnes W M. 1992. The fidelity of taq polymerase catalyzing PCR is improved by an N-terminal deletion. Gene 112:29-35.

Kermekchiev M B, Tzekov A, Barnes W M. 2003. Cold-sensitive mutants of Taq DNA polymerase provide a hot start PCR. Nucleic Acids Res. 31:6139-47.

Tabor S, Richardson C C. 1995. A single residue in DNA polymerises of the *E. coli* DNA polymerase I family is critical for distinguishing between deoxy- and dideoxyribonucleotides. Proc. Natl. Acad. Sci., USA 92:6339-43.

Tawfik D S, Griffiths A D. 1998. Man-made cell-like compartments for molecular evolution. Nature Biotech. 16:652-56.

Ghadessy F J, Ong J L, Holliger P. 2001. Direct evolution of polymerase function by compartmentalized self-replication. Proc. Natl. Acad. Sci., USA 98:4552-57.

Barnes W M. 1994. PCR amplification of up to 35 kb DNA with high fidelity and high yield from bacteriophage templates. Proc. Natl. Acad. Sci., USA 91:2216-20.

Barnes W M. 1994. Tips and tricks for long and accurate PCR. TIBS 19:342-46.

Ausubel F M, Brent R, Kingston R E, Moore D D et al. 1987. Current Protocols In Molecular Biology. John Wiley & Sons, New York.

Sambrook J. 1989. Molecular cloning: a laboratory manual. Cold Spring Harbor Laboratory, Cold Spring Harbor.

Barnes W M. Jul. 25, 1995. U.S. Pat. No. 5,436,149, Thermostable DNA polymerase with enhanced thermostability and enhanced length and efficiency of primer extension.

Barnes W M. Apr. 1, 1997. U.S. Pat. No. 5,616,494, *Thermus aquaticus* DNA polymerase lacking the n-terminal 235 amino acids of taq DNA polymerase.

Scalice E R, Sharkey D J, Daiss J L. 1994. Monoclonal antibodies prepared against the DNA polymerase from *Thermus aquaticus* are potent inhibitors of enzyme activity. J. Immunol. Methods 172:147-63.

Sharkey D J, Scalice E R, Christy K G Jr, Atwood S M, Daiss J L. 1994. Antibodies as thermolabile switches: high temperature triggering for the polymerase chain reaction. Biotechnology 12:506-9.

Kellogg D E, Rybalkin I, Chen S, Mukhamedova N, Vlasik T, Siebert P D, Chenchik A. 1994. TaqStart Antibody: "hot start" PCR facilitated by a neutralizing monoclonal antibody directed against Taq DNA polymerase. Biotechniques 16:1134-7.

Baskaran N, Kandpal R P, Bhargava A K, Glynn M W, Bale A, Weissman S M. 1996. Uniform amplification of a mixture of deoxyribonucleic acids with varying GC content. Genome Res. 6:633-8.

What is claimed is:

1. A method of amplifying a nucleic acid molecule comprising:
   forming a reaction mixture comprising a target nucleic acid molecule and at least one polymerase, the at least one polymerase comprising
   (i) SEQ ID NO: 30 or a variant thereof having at least 95% sequence identity to SEQ ID NO: 30, wherein position 708 of the variant of SEQ ID NO: 30 is leucine (L) or lysine (K) and the variant of SEQ ID NO: 30 has blood resistant polymerase activity or blood resistant polymerase activity and faster elongating polymerase activity or
   a fragment of (i) comprising leucine or lysine at the position corresponding to position 708 of SEQ ID NO: 30, wherein the fragment has blood resistant polymerase activity or blood resistant polymerase activity and faster elongating polymerase activity; and
   amplifying the target nucleic acid molecule in the reaction mixture.

2. The method of claim 1, wherein the reaction mixture comprises a sample comprising whole blood or a blood fraction.

3. The method of claim 2, wherein the sample comprising whole blood or a blood fraction comprises the target nucleic acid molecule.

4. The method of claim 2, wherein the whole blood or blood fraction comprises greater than about 3% of the reaction mixture.

5. The method of claim 3, wherein the whole blood or blood fraction comprises a range from about 5% to about 20% of the reaction mixture.

6. The method of claim 2, wherein the whole blood or blood fraction is untreated, EDTA-treated, or heparinized.

7. The method of claim 1, wherein the reaction mixture comprises at least a second polymerase.

8. The method of claim 7, wherein the second polymerase comprises 3'-exonuclease activity.

9. The method of claim 7, wherein the second polymerase is selected from the group consisting of Vent DNA polymerase, Deep Vent DNA polymerase, Pfu DNA polymerase, and Pwu DNA polymerase.

10. The method of claim 2, wherein:
    forming the reaction mixture comprises (a) adding a nucleic acid amplification cocktail to a reaction vessel, the amplification cocktail comprising the at least one polymerase and (b) adding a sample comprising whole blood or a blood fraction to the reaction vessel;
    amplifying the target nucleic acid molecule in the reaction mixture comprises performing a thermal cycling program;
    the whole blood or blood fraction is layered beneath the nucleic acid amplification cocktail regardless of the order of addition of the nucleic acid amplification cocktail and the sample comprising whole blood or blood fraction to the reaction vessel; and
    the nucleic acid amplification cocktail and the sample comprising whole blood or blood fraction are not mixed before thermal cycling.

11. The method of claim 2, wherein:
    forming the reaction mixture comprises (a) adding a first volume component to a reaction vessel, the first volume component comprising a nucleic acid amplification cocktail lacking an essential constituent required for amplification activity and (b) adding a second volume component to the reaction vessel, the second volume component being heavier than the first volume component and the second volume component comprising the essential constituent required for amplification activity;

the second volume component is layered beneath the first volume component regardless of the order of addition of the second volume component and the first volume component to the reaction vessel; and the second volume component and the first volume component are not mixed before amplification is initiated.

12. The method of claim 11, wherein the second volume component comprises at least one of the target nucleic acid molecule, the sample comprising whole blood or blood fraction, the at least one polymerase, a magnesium salt, deoxynucleotide triphosphates, sucrose or sorbitol, or betaine.

13. The method of claim 1, wherein the at least one polymerase comprises SEQ ID NO: 30 (FL-12).

14. The method of claim 1, wherein:

the at least one polymerase comprises the variant having at least 95% sequence identity to SEQ ID NO: 30; wherein position 708 of the variant of SEQ ID NO: 30 is leucine (L) or lysine (K) and the variant of SEQ ID NO: 30 has blood resistant polymerase activity or blood resistant polymerase activity and faster elongating polymerase activity.

15. The method of claim 1, wherein:

the at least one polymerase comprises the variant having at least 95% sequence identity to SEQ ID NO: 30, wherein position 609 of the variant of SEQ ID NO: 30 is proline (P), position 626 of the variant of SEQ ID NO: 30 is lysine (K), position 707 of the variant of SEQ ID NO: 30 is leucine (L), and position 708 of the variant of SEQ ID NO: 30 is leucine (L) and the variant of SEQ ID NO: 30 has blood resistant polymerase activity or blood resistant polymerase activity and faster elongating polymerase activity.

16. The method of claim 1, wherein the at least one polymerase comprises:

(i) the variant having at least 95% sequence identity to SEQ ID NO: 30, wherein position 609 of the variant of SEQ ID NO: 30 is leucine (L), position 626 of the variant of SEQ ID NO: 30 is lysine (K), position 707 of the variant of SEQ ID NO: 30 is leucine (L), and position 708 of the variant of SEQ ID NO: 30 is lysine (K); or (ii) a polypeptide of SEQ ID NO: 28 (FL-10).

17. The method of claim 1, wherein the fragment of (ii) comprises position 279 to position 832 of SEQ ID NO: 30.

18. The method of claim 1, wherein:

the fragment (ii) has at least 95% sequence identity to position 279 to position 832 of SEQ ID NO: 30; wherein position 708 of the fragment of (ii) is leucine (L) or lysine (K) and the fragment has blood resistant polymerase activity or blood resistant polymerase activity and faster elongating polymerase activity.

19. The method of claim 1, wherein the at least one polymerase comprises:

(i) a fragment having at least 95% sequence identity to position 279 to position 832 of SEQ ID NO: 30, wherein the position of the fragment corresponding to position 609 of SEQ ID NO: 30 is proline (P), the position of the fragment corresponding to position 626 of SEQ ID NO: 30 is lysine (K), the position of the fragment corresponding to position 707 of SEQ ID NO: 30 is leucine (L), and the position of the fragment corresponding to position 708 of SEQ ID NO: 30 is leucine (L); or (ii) a polypeptide of SEQ ID NO: 24 (KT-12).

20. The method of claim 1, wherein the at least one polymerase comprises:

(i) a fragment having at least 95% sequence identity to position 279 to position 832 of SEQ ID NO: 30, wherein the position of the fragment corresponding to position 609 of SEQ ID NO: 30 is leucine (L), the position of the fragment corresponding to position 626 of SEQ ID NO: 30 is lysine (K), the position of the fragment corresponding to position 707 of SEQ ID NO: 30 is leucine (L), and the position of the fragment corresponding to position 708 of SEQ ID NO: 30 is lysine (K); or (ii) a polypeptide of SEQ ID NO: 20 (KT-10).

* * * * *

SEQUENCE LISTING

<160> NUMBER OF SEQ ID NOS: 30

<210> SEQ ID NO 1
<211> LENGTH: 1682
<212> TYPE: DNA
<213> ORGANISM: Thermus aquaticus

<400> SEQUENCE: 1

```
atggggctcc tccacgagtt cggccttctg gaaagcccca aggccctgga ggaggccccc      60
tggcccccgc cggaaggggc cttcgtgggc tttgtgcttt cccgcaagga gcccatgtgg     120
gccgatcttc tggccctggc cgccgccagg ggggccggg tccaccgggc ccccgagcct      180
tataaagccc tcagggacct gaaggaggcg cgggggcttc tcgccaaaga cctgagcgtt     240
ctggccctga gggaaggcct tggcctcccg cccggcgacg accccatgct cctcgcctac     300
ctcctggacc cttccaacac cacccccgag ggggtggccc ggcgctacgg cggggagtgg     360
acggaggagg cgggggagcg ggccgccctt tccgagaggc tcttcgccaa cctgtggggg     420
aggcttgagg gggaggagag gctcctttgg ctttaccggg aggtggagag gcccctttcc     480
gctgtcctgg cccacatgga ggccacgggg gtgcgcctgg acgtggccta tctcagggcc     540
ttgtccctgg aggtggccga ggagatcgcc cgcctcgagg ccgaggtctt ccgcctggcc     600
ggccacccct tcaacctcaa ctcccgggac cagctggaaa gggtcctctt tgacgagcta     660
gggcttcccg ccatcggcaa gacggagaag accggcaagc gctccaccag cgccgccgtc     720
```

```
ctggaggccc tccgcgaggc ccaccccatc gtggagaaga tcctgcagta ccggagctc      780 accaagctga agagcaccta cattgacccc ttgccggacc tcatccaccc caggacgggc      840
cgcctccaca cccgcttcaa ccagacggca acggccacgg gcaggctaag tagctccgat      900
cccaacctcc agaacatccc cgtccgcacc ccgcttgggc agaggatccg ccgggccttc      960
atcgccgagg aggggtggct attggtggcc ctggactata gccagataga gctcaggttg     1020
ctggcccacc tctccggcga cgagaacctg atccgggtct tccaggaggg gcgggacatc     1080
cacacggaga ccgccagctg gatgttcggc gtccccgggg aggccgtgga ccccctgatg     1140
cgccgggcgg ccaagaccat caacttcggg gtcctctacg gcatgtcggc ccaccgcctc     1200
tcccaggagc tagccatccc ttacgaggag gcccaggcct tcattgagcg ctactttcag     1260
agcttcccca aggtgcgggc ctggattgag aagaccctgg aggagggcag gaggcggggg     1320
tacgtggaga ccctcttcgg ccgccgccgc tacgtgccag acctagaggc ccgggtgaag     1380
agcgtgcggg aggcggccga gcgcatggcc ttcaacatgc ccgtccaggg caccgccgcc     1440
gacctcatga agctggctat ggtgaagctc ttccccaggc tggaggaaat ggggggccagg     1500 atgctccttc aggtccacga cgagctggtc tcgaggccc caaaagagag gcggaggcc      1560 gtggcccggc tggccaagga ggtcatggag ggggtgtatc ccctggccgt gccccttggag     1620 gtggaggtgg ggatagggga ggactggctc tccgccaagg agtagtaagc ttatcgataa     1680
ta                                                                    1682

<210> SEQ ID NO 2
<211> LENGTH: 554
<212> TYPE: PRT
<213> ORGANISM: Thermus aquaticus

<400> SEQUENCE: 2

Met Gly Leu Leu His Glu Phe Gly Leu Leu Glu Ser Pro Lys Ala Leu
 1               5                  10                  15

Glu Glu Ala Pro Trp Pro Pro Pro Glu Gly Ala Phe Val Gly Phe Val
                20                  25                  30

Leu Ser Arg Lys Glu Pro Met Trp Ala Asp Leu Leu Ala Leu Ala Ala
            35                  40                  45

Ala Arg Gly Gly Arg Val His Arg Ala Pro Glu Pro Tyr Lys Ala Leu
        50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
            180                 185                 190

Glu Ala Glu Val Phe Arg Leu Ala Gly His Pro Phe Asn Leu Asn Ser
```

```
              195                 200                 205
Arg Asp Gln Leu Glu Arg Val Leu Phe Asp Glu Leu Gly Leu Pro Ala
210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                    245                 250                 255

Tyr Arg Glu Leu Thr Lys Leu Lys Ser Thr Tyr Ile Asp Pro Leu Pro
                260                 265                 270

Asp Leu Ile His Pro Arg Thr Gly Arg Leu His Thr Arg Phe Asn Gln
            275                 280                 285

Thr Ala Thr Ala Thr Gly Arg Leu Ser Ser Ser Asp Pro Asn Leu Gln
        290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Glu Asn Leu Ile Arg
                340                 345                 350

Val Phe Gln Glu Gly Arg Asp Ile His Thr Glu Thr Ala Ser Trp Met
            355                 360                 365

Phe Gly Val Pro Arg Glu Ala Val Asp Pro Leu Met Arg Arg Ala Ala
        370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Ile Glu Lys Thr
                420                 425                 430

Leu Glu Glu Gly Arg Arg Arg Gly Tyr Val Glu Thr Leu Phe Gly Arg
            435                 440                 445

Arg Arg Tyr Val Pro Asp Leu Glu Ala Arg Val Lys Ser Val Arg Glu
450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
                500                 505                 510

Ala Pro Lys Glu Arg Ala Glu Ala Val Ala Arg Leu Ala Lys Glu Val
            515                 520                 525

Met Glu Gly Val Tyr Pro Leu Ala Val Pro Leu Glu Val Glu Val Gly
        530                 535                 540

Ile Gly Glu Asp Trp Leu Ser Ala Lys Glu
545                 550

<210> SEQ ID NO 3
<211> LENGTH: 1682
<212> TYPE: DNA
<213> ORGANISM: Thermus aquaticus

<400> SEQUENCE: 3
atggggctcc tccacgagtt cggccttctg gaaagcccca aggccctgga ggaggccccc      60 tggccccgc cggaaggggc cttcgtgggc tttgtgcttt cccgcaagga gcccatgtgg     120
```

```
gccgatcttc tggccctggc cgccgccagg ggggccgggg tccaccgggc ccccgagcct      180
tataaagccc tcagggacct gaaggaggcg cggggggcttc tcgccaaaga cctgagcgtt      240
ctggccctga gggaaggcct tggcctcccg cccggcgacg accccatgct cctcgcctac      300
ctcctggacc cttccaacac cacccccgag ggggtggccc ggcgctacgg cggggagtgg      360
acggaggagg cggggggagcg ggccgccctt tccgagaggc tcttcgccaa cctgtggggg      420
aggcttgagg gggaggagag gctcctttgg ctttaccggg aggtggagag gccccttttcc      480
gctgtcctgg cccacatgga ggcacgggg gtgcgcctgg acgtggccta tctcagggcc      540
ttgtccctgg aggtggccga ggagatcgcc cgcctcgagg ccgaggtctt ccgcctggcc      600
ggccacccct tcaacctcaa ctcccgggac cagctggaaa gggtcctctt tgacgagcta      660
gggcttcccg ccatcggcaa gacggagaag accggcaagc gctccaccag cgccgccgtc      720
ctggaggccc tccgcgaggc ccaccccatc gtggagaaga tcctgcagta ccgggagctc      780
accaagctga gagcaccta cattgacccc ttgccggacc tcatccaccc caggacgggc      840
cgcctccaca cccgcttcaa ccagacggcc acggccacgg gcaggctaag tagctccgat      900
cccaacctcc agaacatccc cgtccgcacc ccgcttgggc agaggatccg ccgggccttc      960
atcgccgagg agggggtggct attggtggcc ctggactata gccagataga gctcagggtg     1020
ctggcccacc tctccggcga cgagaacctg atccgggtct tccaggaggg gcgggacatc     1080
cacacggaga ccgccagctg gatgttcggc gtccccccggg aggccgtgga ccccctgatg     1140
cgccgggcgg ccaagaccat caacttcggg gtcctctacg gcatgtcggc ccaccgcctc     1200
tcccaggagc tagccatccc ttacgaggag gcccaggcct tcattgagcg ctactttcag     1260
agcttcccca aggtgcgggc ctggcttgtg aagaccctgg aggagggcag gaggcggggg     1320
tacgtggaga ccctcttcgg ccgccgccgc tacgtgccag acctagaggc ccgggtgaag     1380
agcgtgcggg aggcggccga gcgcatggcc ttcaacatgc ccgtccaggg caccgccgcc     1440
gacctcatga agctggctat ggtgaagctc ttccccaggc tggaggaaat ggggggccagg     1500
atgctccttc aggtccacga cgagctggtc ctcgaggccc caaaagagag gcgcgaaggcc     1560
gtggcccggc tggccaagga ggtcatggag ggggtgtatc ccctggccgt gcccctggag     1620
gtggaggtgg ggatagggga ggactggctc tccgccaagg agtagtaagc ttatcgatga     1680
ta                                                                     1682
```

<210> SEQ ID NO 4
<211> LENGTH: 554
<212> TYPE: PRT
<213> ORGANISM: Thermus aquaticus

<400> SEQUENCE: 4

```
Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
            20                  25                  30

Leu Ser Arg Lys Glu Pro Met Trp Ala Asp Leu Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95
```

```
Leu Leu Ala Tyr Leu Leu Asp Pro Ser Asn Thr Thr Pro Glu Gly Val
                100                 105                 110

Ala Arg Arg Tyr Gly Gly Glu Trp Thr Glu Ala Gly Glu Arg Ala
        115                 120                 125

Ala Leu Ser Glu Arg Leu Phe Ala Asn Leu Trp Gly Arg Leu Glu Gly
        130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
        180                 185                 190

Glu Ala Glu Val Phe Arg Leu Ala Gly His Pro Phe Asn Leu Asn Ser
        195                 200                 205

Arg Asp Gln Leu Glu Arg Val Leu Phe Asp Glu Leu Gly Leu Pro Ala
        210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
        260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
        290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Glu Asn Leu Ile Arg
        340                 345                 350

Val Phe Gln Glu Gly Arg Asp Ile His Thr Glu Thr Ala Ser Trp Met
        355                 360                 365

Phe Gly Val Pro Arg Glu Ala Val Asp Pro Leu Met Arg Arg Ala Ala
        370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Leu Val Lys Thr
        420                 425                 430

Leu Glu Glu Gly Arg Arg Gly Tyr Val Glu Thr Leu Phe Gly Arg
        435                 440                 445

Arg Arg Tyr Val Pro Asp Leu Glu Ala Arg Val Lys Ser Val Arg Glu
        450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
        500                 505                 510

Ala Pro Lys Glu Arg Ala Glu Ala Val Ala Arg Leu Ala Lys Glu Val
        515                 520                 525
```

Met Gly Val Tyr Pro Leu Ala Val Pro Leu Glu Val Glu Val Gly
    530                 535                 540

Ile Gly Glu Asp Trp Leu Ser Ala Lys Glu
545                 550

<210> SEQ ID NO 5
<211> LENGTH: 1682
<212> TYPE: DNA
<213> ORGANISM: Thermus aquaticus

<400> SEQUENCE: 5

| | | | | |
|---|---|---|---|---|
| atggggctcc | tccacgagtt | cggccttctg | gaaagcccca | aggccctgga ggaggccccc | 60 |
| tggcccccgc | cggaagggc | cttcgtgggc | tttgtgcttt | cccgcaagga gcccatgtgg | 120 |
| gccgatcttc | tggccctggc | cgccgccagg | ggggccggg | tccaccgggc cccgagcct | 180 |
| tataaagccc | tcagggacct | gaaggaggcg | cggggcttc | tcgccaaaga cctgagcgtt | 240 |
| ctggccctga | ggaaggcct | tggcctcccg | cccggcgacg | accccatgct cctcgcctac | 300 |
| ctcctggacc | cttccaacac | cacccccgag | ggggtggccc | ggcgctacgg cggggagtgg | 360 |
| acggaggagc | cggggagcg | ggccgccctt | tccgagaggc | tcttcgccaa cctgtggggg | 420 |
| aggcttgagg | gggaggagag | gctccttttgg | ctttaccggg | aggtggagag ccccttttcc | 480 |
| gctgtcctgg | cccacatgga | ggccacgggg | gtgcgcctgg | acgtggccta tctcagggcc | 540 |
| ttgtccctgg | aggtggccga | ggagatcgcc | cgcctcgagg | ccgaggtctt ccgcctggcc | 600 |
| ggccaccccct | tcaacctcaa | ctcccgggac | cagctggaaa | gggtcctctt tgacgagcta | 660 |
| gggcttcccg | ccatcggcaa | gacggagaag | accggcaagc | gctccaccag cgccgccgtc | 720 |
| ctggaggccc | tccgcgaggc | ccaccccatc | gtggagaaga | tcctgcagta ccgggagctc | 780 |
| accaagctga | gagcaccta | cattgacccc | ttgccggacc | tcatccaccc caggacgggc | 840 |
| cgcctccaca | cccgcttcaa | ccagacggcc | acggccacgg | gcaggctaag tagctccgat | 900 |
| cccaacctcc | agaacatccc | cgtccgcacc | ccgcttgggc | agaggatccg ccgggccttc | 960 |
| atcgccgagg | aggggtggct | attggtggcc | ctggactata | gccagataga gctcagggtg | 1020 |
| ctggcccacc | tctccggcga | caagaacctg | atccgggtct | tccaggaggg gcgggacatc | 1080 |
| cacacggaga | ccgccagctg | gatgttcggc | gtccccgggg | aggccgtgga ccccctgatg | 1140 |
| cgccgggcgg | ccaagaccat | caacttcggg | gtcctctacg | gcatgtcggc ccaccgcctc | 1200 |
| tcccaggagc | tagccatccc | ttacgaggag | gcccaggcct | tcattgagcg ctactttcag | 1260 |
| agcttcccca | aggtgcgggc | ctggcttgg | aagaccctgg | aggagggcag gaggcggggg | 1320 |
| tacgtggaga | ccctcttcgg | ccgccgccgc | tacgtgccag | acctagaggc ccgggtgaag | 1380 |
| agcgtgcggg | aggcggccga | cgcatggcc | ttcaacatgc | ccgtccaggg caccgccgcc | 1440 |
| gacctcatga | agctggctat | ggtgaagctc | ttccccaggc | tggaggaaat ggggggccagg | 1500 |
| atgctccttc | aggtccacga | cgagctggtc | ctcgaggccc | caaaagagag gcggaggc | 1560 |
| gtggcccggc | tgccaaggga | ggtcatggag | ggggtgtatc | ccctggccgt gccccctggag | 1620 |
| gtggaggtgg | ggataggga | ggactggctc | tccgccaagg | agtagtaagc ttatcgatga | 1680 |
| ta | | | | | 1682 |

<210> SEQ ID NO 6
<211> LENGTH: 554
<212> TYPE: PRT
<213> ORGANISM: Thermus aquaticus

<400> SEQUENCE: 6

```
Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
            20              25                  30

Leu Ser Arg Lys Glu Pro Met Trp Ala Asp Leu Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
                100                 105                 110

Ala Arg Arg Tyr Gly Gly Glu Trp Thr Glu Glu Ala Gly Glu Arg Ala
            115                 120                 125

Ala Leu Ser Glu Arg Leu Phe Ala Asn Leu Trp Gly Arg Leu Glu Gly
        130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
                180                 185                 190

Glu Ala Glu Val Phe Arg Leu Ala Gly His Pro Phe Asn Leu Asn Ser
            195                 200                 205

Arg Asp Gln Leu Glu Arg Val Leu Phe Asp Glu Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
                260                 265                 270

Asp Leu Ile His Pro Arg Thr Gly Arg Leu His Thr Arg Phe Asn Gln
                275                 280                 285

Thr Ala Thr Ala Thr Gly Arg Leu Ser Ser Asp Pro Asn Leu Gln
    290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Lys Asn Leu Ile Arg
            340                 345                 350

Val Phe Gln Glu Gly Arg Asp Ile His Thr Glu Thr Ala Ser Trp Met
        355                 360                 365

Phe Gly Val Pro Arg Glu Ala Val Asp Pro Leu Met Arg Arg Ala Ala
    370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Leu Trp Lys Thr
```

```
                    420                 425                 430
Leu Glu Glu Gly Arg Arg Arg Gly Tyr Val Glu Thr Leu Phe Gly Arg
            435                 440                 445

Arg Arg Tyr Val Pro Asp Leu Glu Ala Arg Val Lys Ser Val Arg Glu
        450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
            530                 535                 540

Ile Gly Glu Asp Trp Leu Ser Ala Lys Glu
545                 550
```

```
<210> SEQ ID NO 7
<211> LENGTH: 33
<212> TYPE: DNA
<213> ORGANISM: Artificial Sequence
<220> FEATURE:
<223> OTHER INFORMATION: Synthetic primer

<400> SEQUENCE: 7
tggaacaaga tggattatca agtgtcaagt cca                                    33

<210> SEQ ID NO 8
<211> LENGTH: 33
<212> TYPE: DNA
<213> ORGANISM: Artificial Sequence
<220> FEATURE:
<223> OTHER INFORMATION: Synthetic primer

<400> SEQUENCE: 8
agaagagctg agacatccgt tcccctacaa gaa                                    33

<210> SEQ ID NO 9
<211> LENGTH: 33
<212> TYPE: DNA
<213> ORGANISM: Artificial Sequence
<220> FEATURE:
<223> OTHER INFORMATION: Synthetic primer

<400> SEQUENCE: 9
aggctgtgta tgaaaactaa gccatgtgca caa                                    33

<210> SEQ ID NO 10
<211> LENGTH: 33
<212> TYPE: DNA
<213> ORGANISM: Artificial Sequence
<220> FEATURE:
<223> OTHER INFORMATION: Synthetic primer

<400> SEQUENCE: 10
gcagcggcag gaccagcccc aagatgacta tct                                    33

<210> SEQ ID NO 11
<211> LENGTH: 36
<212> TYPE: DNA
<213> ORGANISM: Artificial Sequence
<220> FEATURE:
```

<223> OTHER INFORMATION: Synthetic primer

<400> SEQUENCE: 11
gagccatggt cctcctccac gagttcggcc ttctgg                36

<210> SEQ ID NO 12
<211> LENGTH: 31
<212> TYPE: DNA
<213> ORGANISM: Artificial Sequence
<220> FEATURE:
<223> OTHER INFORMATION: Synthetic primer

<400> SEQUENCE: 12
cggtccgaaa gcttctatca ctccttggcg g                    31

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
ggctgtgata gaggcttgtc tata                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
ctggcctgca catcagaaaa gact                            24

<210> SEQ ID NO 15
<211> LENGTH: 30
<212> TYPE: DNA
<213> ORGANISM: Artificial Sequence
<220> FEATURE:
<223> OTHER INFORMATION: Synthetic primer

<400> SEQUENCE: 15
aggtacctgg ctgtcgtcca tgctgtgttt                      30

<210> SEQ ID NO 16
<211> LENGTH: 30
<212> TYPE: DNA
<213> ORGANISM: Artificial Sequence
<220> FEATURE:
<223> OTHER INFORMATION: Synthetic primer

<400> SEQUENCE: 16
gatgatgggg ttgatgcagc agtgcgtcat                      30

<210> SEQ ID NO 17
<211> LENGTH: 34
<212> TYPE: DNA
<213> ORGANISM: Artificial Sequence
<220> FEATURE:
<223> OTHER INFORMATION: Synthetic primer

<400> SEQUENCE: 17
ggaagtacag ctcagagttc tgcagcaccc ctgc                 34

<210> SEQ ID NO 18

```
<211> LENGTH: 31
<212> TYPE: DNA
<213> ORGANISM: Artificial Sequence
<220> FEATURE:
<223> OTHER INFORMATION: Synthetic primer

<400> SEQUENCE: 18
gatgcgaaac tgaggctggc tgtactgtct c                              31

<210> SEQ ID NO 19
<211> LENGTH: 1682
<212> TYPE: DNA
<213> ORGANISM: Thermus aquaticus

<400> SEQUENCE: 19
atggggctcc tccacgagtt cggccttctg gaaagcccca aggccctgga ggaggccccc    60
tggcccccgc cggaaggggc cttcgtgggc tttgtgcttt cccgcaagga gcccatgtgg   120
gccgatcttc tggccctggc cgccgccagg ggggccgggt ccaccgggcc cccgagcct   180 tataaagccc tcagggacct gaaggaggcg cgggggcttc tcgccaaaga cctgagcgtt   240
ctggccctga gggaaggcct tggcctcccg cccggcgacg accccatgct cctcgcctac   300
ctcctggacc cttccaacac caccccgag ggggtggccc ggcgctacgg cggggagtgg   360
acggaggagg cgggggagcg gccgcccctt tccgagaggc tcttcgccaa cctgtggggg   420
aggcttgagg gggaggagag gctcctttgg ctttaccggg aggtggagag ccccctttcc   480
gctgtcctgg cccacatgga ggccacgggg gtgcgcctgg acgtggccta tctcagggcc   540
ttgtccctgg aggtggccga ggagatcgcc cgcctcgagg ccgaggtctt ccgcctggcc   600
ggccaccccc tcaacctcaa ctcccgggac cagctggaaa gggtcctctt tgacgagcta   660
gggcttcccg ccatcggcaa gacggagaag accggcaagc gctccaccag cgccgccgtc   720
ctggaggccc tccgcgaggc ccaccccatc gtggagaaga tcctgcagta ccggagctc   780 accaagctga gagcaccta cattgacccc ttgccggacc tcatccaccc caggacgggc   840
cgcctccaca cccgcttcaa ccagacggcc acggccacgg gcaggctaag tagctccgat   900
cccaacctcc agaacatccc cgtccgcacc ccgcttgggc agaggatccg ccgggccttc   960
atcgccgagg aggggtggct attggtggcc ctggactata gccagataga gctcagggtg  1020
ctggcccacc tctccggcga caagaacctg atccgggtct ccaggagggg gcgggacatc  1080
cacacggaga ccgccagctg gatgttcggc gtccccggg aggccgtgga ccccctgatg  1140
cgccgggcgg ccaagaccat caacttcggg gtcctctacg gcatgtcggc ccaccgcctc  1200
tcccaggagc tagccatccc ttacgaggag gcccaggcct tcattgagcg ctactttcag  1260
agcttcccca aggtgcgggc ctggcttaag aagaccctgg aggagggcag gaggcggggg  1320
tacgtggaga ccctcttcgg ccgccgccgc tacgtgccag acctagaggc ccgggtgaag  1380
agcgtgcggg aggcggccga gcgcatggcc ttcaacatgc ccgtccaggg caccgccgcc  1440
gacctcatga agctggctat ggtgaagctc ttccccaggc tggaggaaat ggggggccagg  1500 atgctccttc aggtccacga cgagctggtc ctcgaggccc caaaagagag gcggaggcc  1560 gtggcccggc tggccaagga ggtcatggag ggggtgtatc ccctggccgt gccccctggag  1620 gtggaggtgg ggataggga ggactggctc tccgccaagg agtagtaagc ttatcgatga  1680
ta                                                                 1682

<210> SEQ ID NO 20
<211> LENGTH: 554
<212> TYPE: PRT
```

<213> ORGANISM: Thermus aquaticus

<400> SEQUENCE: 20

```
Met Gly Leu Leu His Glu Phe Gly Leu Leu Glu Ser Pro Lys Ala Leu
1               5                   10                  15

Glu Glu Ala Pro Trp Pro Pro Gly Ala Phe Val Gly Phe Val
            20                  25                  30

Leu Ser Arg Lys Glu Pro Met Trp Ala Asp Leu Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
            180                 185                 190

Glu Ala Glu Val Phe Arg Leu Ala Gly His Pro Phe Asn Leu Asn Ser
        195                 200                 205

Arg Asp Gln Leu Glu Arg Val Leu Phe Asp Glu Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
    290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Lys Asn Leu Ile Arg
            340                 345                 350

Val Phe Gln Glu Gly Arg Asp Ile His Thr Glu Thr Ala Ser Trp Met
        355                 360                 365

Phe Gly Val Pro Arg Glu Ala Val Asp Pro Leu Met Arg Arg Ala Ala
    370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
```

```
                          405                 410                 415
Arg Tyr Phe Gln Ser Phe Pro Lys Val Arg Ala Trp Leu Lys Lys Thr
                420                 425                 430

Leu Glu Glu Gly Arg Arg Gly Tyr Val Glu Thr Leu Phe Gly Arg
            435                 440                 445

Arg Arg Tyr Val Pro Asp Leu Glu Ala Arg Val Lys Ser Val Arg Glu
        450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
                500                 505                 510

Ala Pro Lys Glu Arg Ala Glu Ala Val Ala Arg Leu Ala Lys Glu Val
            515                 520                 525

Met Glu Gly Val Tyr Pro Leu Ala Val Pro Leu Glu Val Glu Val Gly
        530                 535                 540

Ile Gly Glu Asp Trp Leu Ser Ala Lys Glu
545                 550

<210> SEQ ID NO 21
<211> LENGTH: 1682
<212> TYPE: DNA
<213> ORGANISM: Thermus aquaticus

<400> SEQUENCE: 21
atggggctcc tccacgagtt cggccttctg gaaagcccca aggccctgga ggaggccccc    60 tggccccgc cggaaggggc cttcgtgggc tttgtgcttt cccgcaagga gcccatgtgg   120
gccgatcttc tggccctggc cgccgccagg ggggccgggt ccaccgggc ccccgagcct   180 tataaagccc tcagggacct gaaggaggcg cggggcttc tcgccaaaga cctgagcgtt   240
ctggccctga gggaaggcct tggcctcccg cccggcgacg accccatgct cctcgcctac   300
ctcctggacc cttccaacac cacccccgag ggggtggccc ggcgctacgg cggggagtgg   360
acggaggagg cgggggagcg ggccgccctt ccgagaggc tcttcgccaa cctgtgggg   420 aggcttgagg gggaggagag gctcctttgg ctttaccggg aggtggagag gcccctttcc   480
gctgtcctgg cccacatgga ggccacgggg gtgcgcctgg acgtggccta tctcagggcc   540
ttgtccctgg aggtggccga ggagatcgcc cgcctcgagg ccgaggtctt ccgcctggcc   600 ggccaccct tcaacctcaa ctcccgggac cagctggaaa gggtcctctt tgacgagcta   660
gggcttcccg ccatcggcaa gacggagaag accggcaagc gctccaccag cgccgccgtc   720
ctggaggccc tccgcgaggc ccaccccatc gtggagaaga tcctgcagta ccgggagctc   780
accaagctga agagcaccta cattgaccc ttgccggacc tcatccaccc caggacgggc   840
cgcctccaca cccgcttcaa ccagacggcc acggccacgg gcaggctaag tagctccgat   900
cccaacctcc agaacatccc cgtccgcacc ccgcttgggc agaggatccg ccgggccttc   960
atcgccgagg agggggtggct attggtggcc ctggactata gccagataga gctcagggtg  1020
ctggcccacc tctccggcga caagaacctg atccgggtct tccaggaggg gcgggacatc  1080
cacacggaga ccgccagctg gatgttcggc atccccggg aggccgtgga ccccctgatg  1140
cgccgggcgg ccaagaccat caacttcggg gtcctctacg gcatgtcggc ccaccgcctc  1200
tcccaggagc tagccatccc ttacgaggag gcccaggcct tcattgagcg ctactttcag  1260
agcttcccca aggtgcgggc ctggcttcg aagaccctgg aggagggcag gaggcgggg   1320
```

-continued

```
tacgtggaga ccctcttcgg ccgccgccgc tacgtgccag acctagaggc ccgggtgaag    1380
agcgtgcggg aggcggccga gcgcatggcc ttcaacatgc ccgtccaggg caccgccgcc    1440
gacctcatga agctggctat ggtgaagctc ttcccccagg ctggaggaaat ggggccagg    1500 atgctccttc aggtccacga cgagctggtc ctcgaggccc aaaagagag gcggaggcc    1560 gtggcccggc tggccaagga ggtcatggag ggggtgtatc ccctggccgt gcccctggag    1620
gtggaggtgg ggatagggga ggactggctc tccgccaagg agtagtaagc ttatcgatga    1680
ta                                                                  1682
```

<210> SEQ ID NO 22
<211> LENGTH: 554
<212> TYPE: PRT
<213> ORGANISM: Thermus aquaticus

<400> SEQUENCE: 22

```
Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
            20                  25                  30

Leu Ser Arg Lys Glu Pro Met Trp Ala Asp Leu Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
            180                 185                 190

Glu Ala Glu Val Phe Arg Leu Ala Gly His Pro Phe Asn Leu Asn Ser
        195                 200                 205

Arg Asp Gln Leu Glu Arg Val Leu Phe Asp Glu Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
    290                 295                 300
```

```
Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Lys Asn Leu Ile Arg
            340                 345                 350

Val Phe Gln Glu Gly Arg Asp Ile His Thr Glu Thr Ala Ser Trp Met
        355                 360                 365

Phe Gly Ile Pro Arg Glu Ala Val Asp Pro Leu Met Arg Arg Ala Ala
370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Leu Ser Lys Thr
            420                 425                 430

Leu Glu Glu Gly Arg Arg Arg Gly Tyr Val Glu Thr Leu Phe Gly Arg
        435                 440                 445

Arg Arg Tyr Val Pro Asp Leu Glu Ala Arg Val Lys Ser Val Arg Glu
    450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
    530                 535                 540

Ile Gly Glu Asp Trp Leu Ser Ala Lys Glu
545                 550

<210> SEQ ID NO 23
<211> LENGTH: 1682
<212> TYPE: DNA
<213> ORGANISM: Thermus aquaticus

<400> SEQUENCE: 23
atggggctcc tccacgagtt cggccttctg gaaagcccca aggccctgga ggaggccccc      60
tggcccccgc cggaagggc cttcgtgggc tttgtgcttt cccgcaagga gcccatgtgg     120
gccgatcttc tggccctggc cgccgccagg ggggccggg tccaccgggc ccccgagcct     180
tataaagccc tcagggacct gaaggaggcg cgggggcttc tcgccaaaga cctgagcgtt     240
ctggccctga gaaggcct tggcctcccg ccggcgacg accccatgct cctcgcctac     300
ctcctggacc cttccaacac caccccgag ggggtggccc ggcgctacgg cggggagtgg     360
acggaggagg cggggagcg ggccgccctt tccgagaggc tcttcgccaa cctgtggggg     420
aggcttgagg gggaggagag gctcctttgg ctttaccggg aggtggagag ccccttttcc     480
gctgtcctgg cccacatgga ggccacgggg gtgcgcctgg acgtggccta tctcagggcc     540
ttgtccctgg aggtggccga ggagatcgcc cgcctcgagg ccgaggtctt ccgcctggcc     600 ggccaccccct tcaacctcaa ctcccgggac cagctggaaa gggtcctctt tgacgagcta     660
gggcttcccg ccatcggcaa gacggagaag accggcaagc gctccaccag cgccgccgtc     720
```

```
ctggaggccc tccgcgaggc ccaccccatc gtggagaaga tcctgcagta ccgggagctc    780
accaagctga agagcaccta cattgacccc ttgccggacc tcatccaccc caggacgggc    840
cgcctccaca cccgcttcaa ccagacggcc acggccacgg gcaggctaag tagctccgat    900
cccaacctcc agaacatccc cgtccgcacc ccgcttgggc agaggatccg ccgggccttc    960
atcgccgagg agggggtggct attggtggcc ccggactata gccagataga gctcagggtg   1020
ctggcccacc tctccggcga caagaacctg atccgggtct tccaggaggg gcgggacatc   1080
cacacggaga ccgccagctg gatgttcggc gtcccccggg aggccgtgga ccccctgatg   1140
cgccgggcgg ccaagaccat caacttcggg gtcctctacg gcatgtcggc caccgcctc    1200 tcccaggagc tagccatccc ttacgaggag gcccaggcct tcattgagcg ctactttcag   1260
agcttcccca aggtgcgggc ctggcttttg aagaccctgg aggagggcag gaggcggggg   1320
tacgtggaga ccctcttcgg ccgccgccgc tacgtgccag acctagaggc ccgggtgaag   1380
agcgtgcggg aggcggccga gcgcatggcc ttcaacatgc ccgtccaggg caccgccgcc   1440
gacctcatga agctggctat ggtgaagctc ttccccaggc tggaggaaat gggggccagg   1500
atgctccttc aggtccacga cgagctggtc ctcgaggccc caaaagagag gcggaggcc    1560 gtggcccggc tggccaagga ggtcatggag ggggtgtatc ccctggccgt gccctggag    1620 gtggaggtgg ggatagggga ggactggctc tccgccaagg agtagtaagc ttatcgatga   1680
ta                                                                  1682

<210> SEQ ID NO 24
<211> LENGTH: 554
<212> TYPE: PRT
<213> ORGANISM: Thermus aquaticus

<400> SEQUENCE: 24

Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
            20                  25                  30

Leu Ser Arg Lys Glu Pro Met Trp Ala Asp Leu Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
            180                 185                 190

Glu Ala Glu Val Phe Arg Leu Ala Gly His Pro Phe Asn Leu Asn Ser
        195                 200                 205
```

Arg Asp Gln Leu Glu Arg Val Leu Phe Asp Glu Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
    290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Pro Asp Tyr Ser Gln Ile
                325                 330                 335

Glu Leu Arg Val Leu Ala His Leu Ser Gly Asp Lys Asn Leu Ile Arg
            340                 345                 350

Val Phe Gln Glu Gly Arg Asp Ile His Thr Glu Thr Ala Ser Trp Met
        355                 360                 365

Phe Gly Val Pro Arg Glu Ala Val Asp Pro Leu Met Arg Arg Ala Ala
    370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Leu Leu Lys Thr
            420                 425                 430

Leu Glu Glu Gly Arg Arg Gly Tyr Val Glu Thr Leu Phe Gly Arg
        435                 440                 445

Arg Arg Tyr Val Pro Asp Leu Glu Ala Arg Val Lys Ser Val Arg Glu
    450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
    530                 535                 540

Ile Gly Glu Asp Trp Leu Ser Ala Lys Glu
545                 550

<210> SEQ ID NO 25
<211> LENGTH: 2506
<212> TYPE: DNA
<213> ORGANISM: Thermus aquaticus

<400> SEQUENCE: 25
atgaggggga tgctgcccct ctttgagccc aagggccggg tcctcctggt ggacggccac      60
cacctggcct accgcacctt ccacgccctg aagggcctca ccaccagccg ggggagccg      120 gtgcaggcgg tctacggctt cgccaagagc ctcctcaagg ccctcaagga ggacgggac      180

```
gcggtgatcg tggtctttga cgccaaggcc ccctccttcc gccacgaggc ctacgggggg      240
tacaaggcgg gccgggcccc cacgccggag gactttcccc ggcaactcgc cctcatcaag      300
gagctggtgg acctcctggg gctggcgcgc ctcgaggtcc cgggctacga ggcggacgac      360
gtcctggcca gcctggccaa gaaggcggaa aaggagggct acgaggtccg catcctcacc      420
gccgacaaag acctttacca gctcctttcc gaccgcatcc acgtcctcca ccccgagggg      480
tacctcatca ccccggcctg gctttgggaa aagtacggcc tgaggcccga ccagtgggcc      540
gactaccggg ccctgaccgg ggacgagtcc gacaaccttc ccggggtcaa gggcatcggg      600
gagaagacgg cgaggaagct tctggaggag tgggggagcc tggaagccct cctcaagaac      660
ctggaccggc tgaagcccgc catccggag aagatcctgg cccacatgga cgatctgaag      720
ctctcctggg acctggccaa ggtgcgcacc gacctgcccc tggaggtgga cttcgccaaa      780
aggcgggagc ccgaccggga gaggcttagg gcctttctgg agaggcttga gtttggcagc      840
ctcctccacg agttcggcct tctggaaagc cccaaggccc tggaggaggc cccctggccc      900
ccgccggaag gggccttcgt gggctttgtg ctttcccgca aggagcccat gtgggccgat      960
cttctggccc tggccgccgc cagggggggc cgggtccacc gggcccccga gccttataaa     1020
gccctcaggg acctgaagga ggcgcggggg cttctcgcca aagacctgag cgttctggcc     1080
ctgagggaag gccttggcct cccgcccggc gacgaccca tgctcctcgc ctacctcctg     1140
gaccctccca acaccacccc cgaggggtg gcccggcgct acggcgggga gtggacggag     1200
gaggcggggg agcgggccgc cctttccgag aggctcttcg ccaacctgtg ggaggcgctt     1260 gaggggagg agaggctcct ttggctttac cgggaggtgg agaggccct ttccgctgtc      1320 ctggcccaca tggaggccac ggggtgcgc ctggacgtgg cctatctcag ggccttgtcc      1380
ctggaggtgg ccgaggagat cgcccgcctc gaggccgagg tcttccgcct ggccggccac     1440
cccttcaacc tcaactcccg ggaccagctg gaaagggtcc tctttgacga gctagggctt     1500
cccgccatcg gcaagacgga gaagaccggc aagcgctcca ccagcgccgc cgtcctggag     1560
gccctccgcg aggcccaccc catcgtggag aagatcctgc agtaccggga gctcaccaag     1620
ctgaagagca cctacattga ccccttgccg gacctcatcc accccaggac gggccgcctc     1680
cacacccgct tcaaccagac ggccacggcc acgggcaggc taagtagctc cgatcccaac     1740
ctccagaaca tccccgtccg caccccgctt gggcagagga tccgccgggc cttcatcgcc     1800
gaggaggggt ggctattggt ggccctggac tatagccaga tagagctcag ggtgctggcc     1860
cacctctccg gcgacgagaa cctgatccgg gtcttccagg aggggcggga catccacacg     1920
gagaccgcca gctggatgtt cggcgtcccc cgggaggccg tggacccct gatgcgccgg     1980 gcggccaaga ccatcaactt cggggtcctc tacggcatgt cggcccaccg cctctcccag     2040
gagctagcca tcccttacga ggaggcccag gccttcattg agcgctactt tcagagcttc     2100
cccaaggtgc gggcctggat tgagaagacc ctggaggagg caggaggcg ggggtacgtg     2160 gagaccctct tcggccgccg ccgctacgtg ccagacctag aggcccgggt gaagagcgtg     2220
cgggaggcgg ccgagcgcat ggccttcaac atgcccgtcc agggcaccgc cgccgacctc     2280
atgaagctgg ctatggtgaa gctcttcccc aggctggagg aaatggggc caggatgctc     2340 cttcaggtcc acgacgagct ggtcctcgag gcccaaaaag agagggcgga ggccgtggcc     2400
cggctggcca aggaggtcat ggaggggtg tatcccctgg ccgtgccct ggaggtggag      2460 gtggggatag gggaggactg gctctccgcc aaggagtgat accacc                    2506
```

-continued

```
<210> SEQ ID NO 26
<211> LENGTH: 832
<212> TYPE: PRT
<213> ORGANISM: Thermus aquaticus

<400> SEQUENCE: 26

Met Arg Gly Met Leu Pro Leu Phe Glu Pro Lys Gly Arg Val Leu Leu
 1               5                  10                  15

Val Asp Gly His His Leu Ala Tyr Arg Thr Phe His Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
     50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
```

```
            385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
            420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
                675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
                740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
            770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
```

```
Leu Glu Val Glu Val Gly Ile Gly Glu Asp Trp Leu Ser Ala Lys Glu
            820                 825                 830
```

<210> SEQ ID NO 27
<211> LENGTH: 2506
<212> TYPE: DNA
<213> ORGANISM: Thermus aquaticus

<400> SEQUENCE: 27

```
atgagggga tgctgcccct ctttgagccc aagggccggg tcctcctggt ggacggccac    60
cacctggcct accgcacctt ccacgccctg aagggcctca ccaccagccg gggggagccg   120
gtgcaggcgg tctacggctt cgccaagagc ctcctcaagg ccctcaagga ggacgggac    180
gcggtgatcg tggtctttga cgccaaggcc cctccttcc gccacgaggc ctacggggg    240
tacaaggcgg gccgggcccc cacgccggag gactttcccc ggcaactcgc cctcatcaag    300
gagctggtgg acctcctggg gctggcgcgc ctcgaggtcc gggctacga gcgacgac    360
gtcctggcca gctggccaa gaaggcgaa aggagggct acgaggtccg catcctcacc    420
gccgacaaag accttacca gctccttcc gaccgcatcc acgtcctcca ccccgagggg    480
tacctcatca ccccggcctg gctttgggaa agtacggcc tgaggcccga ccagtgggcc    540
gactaccggg ccctgaccgg ggacgagtcc gacaacttc ccggggtcaa gggcatcggg    600
gagaagacgc gaggaagct tctggaggag tgggggagcc tggaagccct cctcaagaac    660
ctggaccggc tgaagcccgc catccggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc ccaaggccc tggaggaggc ccctggccc    900
ccgccggaag gggccttcgt gggctttgtg cttttcccgca aggagcccat gtgggccgat    960
cttctgccc tggccgccgc cagggggggc cgggtccacc gggcccccga gccttataaa   1020
gccctcaggg acctgaagga ggcgcggggg cttctcgcca agacctgag cgttctggcc   1080
ctgagggaag gccttggcct cccgccggc gacgacccca tgctcctgc ctacctcctg   1140
gaccttcca acaccacccc cgagggggtg gcccggcgct acggcgggga gtggacggag   1200
gaggcggggg agcgggccgc ccttcccgag aggctcttcg ccaacctgtg ggaggctt   1260
gagggaggg agaggctcct ttggctttac cgggaggtgg agaggcccct ttccgctgtc   1320
ctggcccaca tggaggccac ggggtgcgc ctggacgtgg cctatctcag gccttgcc   1380
ctggaggtgg ccgaggagat cgcccgcctc gaggccgagg tcttccgcct ggccggccac   1440
cccttcaacc tcaactcccg ggaccagctg gaaagggtcc tctttgacga gctagggctt   1500
cccgccatcg gcaagacgga aagaccggc aagcgctcca ccagcgccgc cgtcctggag   1560
gccctccgcg aggcccaccc catcgtggag aagatcctgc agtaccggga gctcaccaag   1620
ctgaagagca cctacattga ccccttgccg gacctcatcc accccaggac gggccgcctc   1680
cacacccgct tcaaccagac ggccacggcc acgggcaggc taagtagctc cgatcccaac   1740
ctccagaaca tcccgtccg cacccgctt ggcagagga tccgccgggc cttcatcgcc   1800
gaggagggt ggctattggt ggccctggac tatagccaga tagagctcag ggtgctggcc   1860
cacctctccg gcgacaagaa cctgatccgg gtcttccagg agggcggga catccacacg   1920
gagaccgcca gctggatgtt cggcgtcccc cgggaggccg tggaccccct gatgcgccgg   1980
gcggccaaga ccatcaactt cggggtcctc tacggcatgt cggcccaccg cctctcccag   2040
gagctagcca tcccttacga ggaggccag gccttcattg agcgctactt tcagagcttc   2100
```

```
cccaaggtgc gggcctggct taagaagacc ctggaggagg gcaggaggcg ggggtacgtg    2160
gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggagggggtg tatccccctgg ccgtgcccct ggaggtggag    2460
gtggggatag ggaggactg gctctccgcc aaggagtgat accacc                    2506
```

<210> SEQ ID NO 28
<211> LENGTH: 832
<212> TYPE: PRT
<213> ORGANISM: Thermus aquaticus

<400> SEQUENCE: 28

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300
```

-continued

```
Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Lys Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Leu Lys Lys Thr Leu Glu Glu Gly Arg Arg Gly Tyr Val
705                 710                 715                 720

Glu Thr Leu Phe Gly Arg Arg Arg Tyr Val Pro Asp Leu Glu Ala Arg
            725                 730                 735
```

```
Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 29
<211> LENGTH: 2506
<212> TYPE: DNA
<213> ORGANISM: Thermus aquaticus

<400> SEQUENCE: 29
```

| | | | | | |
|---|---|---|---|---|---|
| atgaggggga | tgctgccccT | ctttgagccc | aagggccggg | tcctcctggt | ggacggccac    60 |
| cacctggcct | accgcacctt | ccacgccctg | aagggcctca | ccaccagccg | ggggagccg    120 |
| gtgcaggcgg | tctacggctt | cgccaagagc | ctcctcaagg | ccctcaagga | ggacggggac    180 |
| gcggtgatcg | tggtctttga | cgccaaggcc | cctccttcc | gccacgaggc | ctacggggg    240 |
| tacaaggcgg | gccgggcccc | cacgccgag | gactttcccc | ggcaactcgc | cctcatcaag    300 |
| gagctggtgg | acctcctggg | gctggcgcgc | ctcgaggtcc | cgggctacga | ggcggacgac    360 |
| gtcctggcca | gcctggccaa | gaaggcggaa | aaggagggct | acgaggtccg | catcctcacc    420 |
| gccgacaaag | accttttacca | gctcctttcc | gaccgcatcc | acgtcctcca | ccccgaggg    480 |
| tacctcatca | cccccggcctg | gctttgggaa | aagtacggcc | tgaggcccga | ccagtgggcc    540 |
| gactaccggg | ccctgaccgg | ggacgagtcc | gacaaccttc | cggggtcaa | gggcatcggg    600 |
| gagaagacgc | gaggaagct | tctggaggag | tgggggagcc | tggaagccct | cctcaagaac    660 |
| ctggaccggc | tgaagcccgc | catccgggag | aagatcctgg | cccacatgga | cgatctgaag    720 |
| ctctcctggg | acctggccaa | ggtgcgcacc | gacctgcccc | tggaggtgga | cttcgccaaa    780 |
| aggcgggagc | ccgaccggga | gaggcttagg | gcctttctgg | agaggcttga | gtttggcagc    840 |
| ctcctccacg | agttcggcct | tctggaaagc | cccaaggccc | tggaggaggc | cccctggccc    900 |
| ccgccggaag | gggccttcgt | gggctttgtg | ctttcccgca | aggagcccat | gtgggccgat    960 |
| cttctggccc | tggccgccgc | caggggggc | cgggtccacc | gggccccga | gccttataaa    1020 |
| gccctcaggg | acctgaagga | ggcgcgggg | cttctcgcca | aagacctgag | cgttctggcc    1080 |
| ctgaggggaag | gccttggcct | cccgcccggc | gacgaccca | tgctcctcgc | ctacctcctg    1140 |
| gacccttcca | acaccaccc | cgaggggtg | gccggcgct | acggcgggga | gtggacggag    1200 |
| gaggcgggg | agcgggccgc | cctttccgag | aggctcttcg | ccaacctgtg | ggaggctt    1260 |
| gagggggagg | agaggctcct | ttggctttac | cggaggtgg | agaggcccct | ttccgctgtc    1320 |
| ctggcccaca | tggaggccac | ggggtgcgc | ctggacgtgg | cctatctcag | ggccttgtcc    1380 |
| ctggaggtgg | ccgaggagat | cgcccgcctc | gaggccgagt | cttccgcct | ggccggccac    1440 |
| cccttcaacc | tcaactcccg | ggaccagctg | gaaagggtcc | tctttgacga | gctagggctt    1500 |
| cccgccatcg | gcaagacgga | gaagaccggc | aagcgctcca | ccagcgccgc | cgtcctggag    1560 |
| gccctccgcg | aggcccaccc | catcgtggag | aagatcctgc | agtaccggga | gctcaccaag    1620 |

```
ctgaagagca cctacattga ccccttgccg gacctcatcc acccaggac gggccgcctc    1680 cacacccgct tcaaccagac ggccacggcc acgggcaggc taagtagctc cgatcccaac    1740
ctccagaaca tccccgtccg cacccgcgtt gggcagagga tccgccgggc cttcatcgcc    1800 gaggagggt ggctattggt ggccccggac tatagccaga tagagctcag ggtgctggcc     1860
cacctctccg cgacaagaa cctgatccgg gtcttccagg aggggcggga catccacacg     1920
gagaccgcca gctggatgtt cggcgtcccc cgggaggccg tggacccct gatgcgccgg     1980 gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggct tttgaagacc ctggaggagg caggaggcg ggggtacgtg     2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgc tatggtgaa gctcttcccc aggctggagg aaatgggggc caggatgctc     2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag     2460
gtggggatag ggaggactg gctctccgcc aaggagtgat accacc                    2506

<210> SEQ ID NO 30
<211> LENGTH: 832
<212> TYPE: PRT
<213> ORGANISM: Thermus aquaticus

<400> SEQUENCE: 30

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220
```

```
Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Pro Asp Tyr Ser Gln Ile Glu Leu Arg Val Leu Ala His Leu Ser Gly
610                 615                 620

Asp Lys Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
```

```
                      645                 650                 655
Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Leu Leu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```